(12) United States Patent
Dacey et al.

(10) Patent No.: US 10,004,567 B2
(45) Date of Patent: Jun. 26, 2018

(54) STERILE PACKAGING SYSTEMS FOR MEDICAL DEVICES

(71) Applicant: Ethicon, Inc., Somerville, NJ (US)

(72) Inventors: Denise Marie Dacey, Glen Gardner, NJ (US); Xiaole Fan, Annandale, NJ (US); Jared James Patriarca, Glen Gardner, NJ (US); Meredith McHugh Karow, Hatboro, PA (US)

(73) Assignee: Ethicon, Inc., Somerville, NJ (US)

( * ) Notice: Subject to any disclaimer, the term of this patent is extended or adjusted under 35 U.S.C. 154(b) by 0 days. days.

(21) Appl. No.: 15/266,904

(22) Filed: Sep. 15, 2016

(65) Prior Publication Data

US 2018/0071043 A1  Mar. 15, 2018

(51) Int. Cl.
| | |
|---|---|
| *A61B 50/30* | (2016.01) |
| *B65D 5/42* | (2006.01) |
| *B65D 81/02* | (2006.01) |
| *B65D 33/02* | (2006.01) |
| *B65D 77/04* | (2006.01) |
| *B65D 65/40* | (2006.01) |

(52) U.S. Cl.
CPC ............ *A61B 50/30* (2016.02); *B65D 5/4266* (2013.01); *B65D 33/02* (2013.01); *B65D 65/40* (2013.01); *B65D 77/04* (2013.01); *B65D 81/02* (2013.01)

(58) Field of Classification Search
CPC .......... A61B 50/20; A61B 50/30; B65D 5/42; B65D 5/4266; B65D 33/00; B65D 33/02; B65D 65/40; B65D 77/00; B65D 77/04; B65D 81/02
USPC ................................. 206/63.3, 363–370, 438
See application file for complete search history.

(56) References Cited

U.S. PATENT DOCUMENTS

| | | | | |
|---|---|---|---|---|
| 4,014,434 A | * | 3/1977 | Thyen .............. | A61B 17/06138 206/63.3 |
| 4,121,714 A | * | 10/1978 | Daly ........................ | A61L 2/26 206/363 |
| 4,880,117 A | | 11/1989 | Garganese | |
| 4,887,710 A | | 12/1989 | Roshdy et al. | |
| (Continued) | | | | |

FOREIGN PATENT DOCUMENTS

EP           0168172        1/1986

OTHER PUBLICATIONS

Ethilon Sutures by Ethicon [online]; Retrieved Nov. 20, 2017 from URL: http://www.medline.com/product/Ethilon-Sutures-by-Ethicon/Z05-PF45327; 2 pages.

(Continued)

*Primary Examiner* — Bryon Gehman

(57) ABSTRACT

A package for a medical device includes a folder having bottom and top panels, the bottom panel including a leading edge, a trailing edge, and at least one medical device securing element. The top panel has a leading edge, and a trailing edge joined with the trailing edge of the bottom panel. The folder has an unfolded configuration in which the leading edges of the top and bottom panels face in opposite directions, and a folded configuration in which the top panel is folded over the bottom panel so that the leading edges of the top and bottom panels face in the same direction and are aligned with one another. The folder is insertable into a sealable pouch having a seal with a first leg whereby the leading edges of the folder are abutted against the first leg of the seal of the pouch.

22 Claims, 18 Drawing Sheets

(56) References Cited

U.S. PATENT DOCUMENTS

| | | | |
|---|---|---|---|
| 5,219,077 A * | 6/1993 | Transue | A61F 2/0063 |
| | | | 206/438 |
| 5,249,682 A * | 10/1993 | Transue | A61F 2/0063 |
| | | | 206/438 |
| 5,375,717 A * | 12/1994 | Roshdy | B65D 73/0021 |
| | | | 206/363 |
| 5,601,189 A * | 2/1997 | Roshdy | B65D 73/0021 |
| | | | 206/363 |
| D434,982 S | 12/2000 | Zimmerman et al. | |
| D466,011 S | 11/2002 | Garcia | |
| D489,255 S | 5/2004 | Kratzert et al. | |
| D568,172 S | 5/2008 | Rutjes | |
| D568,173 S | 5/2008 | Rutjes | |
| D600,940 S | 9/2009 | Eliaš | |
| 7,600,634 B2 * | 10/2009 | Malinowski | A61B 17/06138 |
| | | | 206/63.3 |
| D608,194 S | 1/2010 | Gajardo | |
| D646,964 S | 10/2011 | Ampadu et al. | |
| D647,395 S | 10/2011 | Mitten et al. | |
| D654,358 S | 2/2012 | Ampadu et al. | |
| D655,153 S | 3/2012 | Mitten et al. | |
| 8,413,810 B2 * | 4/2013 | Merboth | A61B 50/30 |
| | | | 206/438 |
| D699,107 S | 2/2014 | Streich et al. | |
| D743,810 S | 11/2015 | El-Afandi et al. | |
| 9,439,658 B2 * | 9/2016 | Ford | A61B 50/30 |
| D786,059 S | 5/2017 | Lee | |
| D788,582 S | 6/2017 | Sanfilippo et al. | |
| 9,776,783 B2 * | 10/2017 | Nadig | B65D 77/04 |
| 2012/0061262 A1 | 3/2012 | Merboth | |
| 2014/0343553 A1 | 11/2014 | Ford et al. | |

OTHER PUBLICATIONS

Medical Device Packaging [online]; Retrieved Nov. 20, 2017 from URL: http://www.itwlabels.com/Products/Medical-Device-Packaging; 3 pages.

International Search Report issued in corresponding International Application No. PCT/US2017/050903, dated Dec. 18, 2017, 5 pages.

* cited by examiner

STERILE PACKAGING SYSTEMS FOR MEDICAL DEVICES

BACKGROUND OF THE INVENTION

Field of the Invention

The present patent application is generally related to medical devices used during surgical procedures and is more specifically related to sterile packaging systems for medical devices.

Description of the Related Art

During surgical procedures, great care is taken to prevent contamination of the surgical tools and medical devices used during the course of an operation. An operating team typically includes at least one member whose function is to open packages containing surgical tools and medical devices and to present them to a sterile nurse or surgeon in a manner in which they remain in a sterile condition.

In many instances, sealed pouches, such as sealed foil laminate pouches, are used for dispensing sterile medical devices and products. For some medical devices, for example, those that require a high degree of moisture protection, laminate pouches having foil barriers are necessary. Many surgical nurses prefer sealed pouches having large opening flanges with chevron shaped seal lines for ease of aseptically opening and dispensing a medical device in a sterile field. All packages are susceptible to being dropped and mishandled, which results in package integrity failures in certain instances. In addition, foil laminate pouches, especially when used for three-dimensional devices (e.g., a device having a thickness of one or more inches), are more susceptible than two-dimensional foil laminate pouches to package integrity breaches (e.g., holes) when the pouch in certain instances is damaged in processing and handling and then when hard wrinkles subsequently develop, which can break open during transit conditions (e.g., vehicle vibration).

Some medical devices require packaging that provides moisture protection so that excessive moisture does not build up within the sterile package, which could degrade the performance and/or efficacy of the medical device or components contained within the medical device. Typically, a moisture-absorbing card may be used to support the medical device before the card and the medical device are inserted into a pouch, which is sealed to provide a sterile environment inside the package.

FIG. 1 shows a card 20 having medical device securing elements 22A, 22B that are used to secure a medical device 24 over a top surface of the card 20. The card 20 has a leading end 26, a trailing end 28, and a generally rectangular shape. The corners of the card 20 at the leading and trailing ends 26, 28 are rounded. The card may be made of a moisture-absorbing material such as paperboard or of a more robust and inert polyethylene material.

The card 20 is designed to support and secure a medical device 24 having a length, a width, and a thickness. The medical device 24 is not flat and constitutes a three-dimensional (3D) structure that sits atop of the card 20. The medical device 24 is secured to the card 20 via the medical device securing elements 22A, 22B.

Referring to FIGS. 1 and 2A, during a packaging procedure, the leading end 26 of the card 20 is inserted into a sealable foil pouch 30. Referring to FIG. 2A, the foil pouch 30 has three sealed sides 32A, 32B, and 32C, and an open, unsealed side 32D. Typically, the leading end 26 of the card 20 is inserted into the open end 32D of the foil package 30 so that the leading end 26 is adjacent to the sealed end 32B and the trailing end 28 of the card 20 is nearest the open end 32D. A heat seal 34 is then formed adjacent the proximal end of the foil package 30 to fully seal the card 20 and the medical device 24 within the foil pouch 30.

Referring to FIGS. 2A and 2B, during handling and shipment, hard wrinkles or hard pinches may develop in the sealed foil pouch due to the three-dimensional (3D) nature of the medical device positioned within the foil pouch. Hard wrinkling or hard pinches of the foil pouch may be further impacted during shipment of the packages and due to mechanical forces such as vibration. FIGS. 2A and 2B show a foil pouch 30 having wrinkles 36 or hard pinches that may result in the formation of integrity breach holes 38. When testing and evaluating packaging, it has been observed that hard wrinkling of the foil pouch can potentially cause foil integrity failure due to the formation of pin holes 38 or other defects, which destroy the integrity and sterile environment inside the package. The integrity breach holes 38 may have a diameter of about 25-50 microns.

It is believed that one cause of wrinkling of the foil pouch 30 is because the card 20 and the medical device 24 do not completely fill the interior of the foil pouch, which allows the foil pouch to collapse inwardly around the sides of the three-dimensional medical device.

In view of the above-identified deficiencies found in conventional packaging systems for medical devices, there remains a need for packaging systems having medical device cards that completely fill the interior of a foil pouch, that keep the pouch smooth, and that prevent hard wrinkling and pinching of the pouch, which could result in failure of the sterile packages.

SUMMARY OF THE INVENTION

In one embodiment, a package for a medical device includes a folder having a bottom panel and a top panel. In one embodiment, the bottom panel includes a leading edge, a trailing edge, and at least one medical device securing element. In one embodiment, the leading edge of the bottom panel may be a straight edge, or may have various geometric shapes including a chevron shape or a curved shape. In one embodiment, the top panel includes a leading edge, and a trailing edge joined with the trailing edge of the bottom panel to define a folding line extending between the top and bottom panels. In one embodiment, the leading edge of the bottom panel may have various geometric shapes including a straight edge, a chevron shaped edge, or a curved edge. In one embodiment, the folder has an unfolded configuration in which the leading edges of the top and bottom panels face in opposite directions, and a folded configuration in which the top panel is folded over the bottom panel at the folding line and the leading edges of the top and bottom panels face in the same direction and are aligned with one another.

In one embodiment, the bottom panel has first and second lateral edges that extend from the leading edge of the bottom panel to the trailing edge of the bottom panel. In one embodiment, the bottom panel has a first stress relieving slit that extends inwardly from the first lateral edge toward a center of the bottom panel, and a second stress relieving slit that extends inwardly from the second lateral edge toward the center of the bottom panel. In one embodiment, the first and second stress relieving slits are aligned with one another along the length of the bottom panel.

In one embodiment, the top panel has first and second lateral edges that extend from the leading edge of the top panel to the trailing edge of the top panel. In one embodiment, the top panel has a first stress relieving slit that extends inwardly from the first lateral edge toward a center of the top panel, and a second stress relieving slit that extends inwardly from the second lateral edge toward the center of the top panel. In one embodiment, the first and second stress relieving slits of the top panel are aligned with one another along the length of the top panel.

In one embodiment, when the folder is in the folded configuration, the first stress relieving slit of the top panel is aligned with the first stress relieving slit of the bottom panel and the second stress relieving slit of the top panel is aligned with the second stress relieving slit of the bottom panel.

In one embodiment, at least one of the stress relieving slits has an aperture at an inner end thereof. In one embodiment, at least one of the stress relieving slits has an elliptical or ovoid shape. In one embodiment, the outer ends of the stress relieving slits adjacent the lateral edges of the panels are rounded or curved for optimizing pouch smoothness when a folder containing a three-dimensional medical device is inserted into a sealable pouch.

In one embodiment, a medical device is secured on the bottom panel of the folder, and the top panel covers the medical device when the folder is in the folded configuration. In one embodiment, the medical device is a three-dimensional medical device having a length, a width, and a thickness that extends above an inner, major face of the bottom panel.

In one embodiment, the bottom panel has at least one medical device securing element for securing the medical device to the bottom panel. In one embodiment, the at least one medical device securing element is connected with the bottom panel via a fold line that enables the at least one medical device securing element to be folded flat over the bottom panel or extended away from the bottom panel for engaging the medical device. In one embodiment, the bottom panel has first and second medical device securing elements.

In one embodiment, the package includes a sealable pouch including two sheets of material that are joined together by a seal having a first leg that extends adjacent a leading end, and second and third legs that extend adjacent first and second lateral sides of the pouch. In one embodiment, the first leg of the seal has a chevron shape that matches the chevron shaped edges of the top and bottom panels of the folder. In one embodiment, the first leg of the seal has a straight edge that matches the straight leading edges of top and bottom panels of the folder. In other embodiments, the first leg of the seal may have other geometric shapes (e.g., curved) that match the geometric shapes of the leading edges of the top and bottom panels of the folder.

In one embodiment, the folder is disposed in the pouch with the leading edges of the top and bottom panels abutting against the first leg of the seal of the pouch, and the lateral edges of the folder abutting against the respective second and third legs of the pouch seal.

In one embodiment, the seal includes a fourth leg extending between the second and third legs of the seal and adjacent a trailing end of the pouch for sealing the folder and the medical device within the pouch. In one embodiment, the trailing end of the sealed pouch that includes the fourth leg of the seal is folded under the folder to form a pouch fold. In one embodiment, the pouch fold is abutted against the trailing edge of the folder that is disposed within the pouch.

In one embodiment, a package includes a sales unit carton having a leading end and a trailing end, and a plurality of the sealed pouches disposed within the sales unit carton. In one embodiment, each sealed pouch has a folded trailing end that abuts against the trailing edge of the folder where it is folded. In one embodiment, when the sealed and folded pouch is inserted into the sales unit carton, the pouch fold is adjacent the leading end of the sales unit carton and the first leg of the pouch seal is positioned adjacent the trailing end of the sales unit carton.

In one embodiment, the folder is made of hydrophilic materials, paperboard, cardboard, and/or high density polyethylene (HDPE). In one embodiment, when the folder containing the three-dimensional medical device is inserted into the pouch, the outer surfaces of the top and bottom panels of the folder desirably smooth the top and bottom panels of the pouch, which minimizes the likelihood of wrinkles forming in the pouch.

In one embodiment, the pouch may be made of various materials including but not limited to foil, a foil polyester laminate, and a foil nylon laminate.

In one embodiment, a package for a medical device includes a sealed pouch having two sheets of material that are joined together by a seal having a first leg that extends adjacent a leading end of the pouch, second and third legs that extend adjacent first and second lateral sides of the pouch, and a fourth leg that extends adjacent a trailing end of the pouch. In one embodiment, the first leg of the seal has a chevron shape, a curved shape, a straight line, or other geometric shapes.

In one embodiment, the package includes a folder containing a medical device, such as a three-dimensional medical device having a length, a width, and a thickness. In one embodiment, the folder has a bottom panel and a top panel. In one embodiment, the bottom panel has a leading edge and a trailing edge, and the top panel has a leading edge, and a trailing edge joined with the trailing edge of the bottom panel to define a folding line extending between the top and bottom panels. In one embodiment the top panel is folded over the bottom panel at the folding line and the leading edges of the top and bottom panels face in the same direction and are aligned with one another. In one embodiment, the folder containing a three-dimensional medical device is disposed in a sealed pouch with the leading edges of the top and bottom panels of the folder abutting against the first leg of the seal of the sealed pouch.

In one embodiment, the bottom panel has first and second lateral edges that extend from the leading edge of the bottom panel to the trailing edge of the bottom panel, a first stress relieving slit that extends inwardly from the first lateral edge toward a center of the bottom panel, and a second stress relieving slit that extends inwardly from the second lateral edge toward the center of the bottom panel. In one embodiment, the first and second stress relieving slits are aligned with one another along the length of the bottom panel. In one embodiment, the outer ends of the stress relieving slits adjacent the lateral edges of the bottom panel are rounded or curved to optimize pouch smoothness when the folder is inserted into the pouch.

In one embodiment, the top panel has first and second lateral edges that extend from the leading edge of the top panel to the trailing edge of the top panel, a first stress relieving slit that extends inwardly from the first lateral edge toward a center of the top panel, and a second stress relieving slit that extends inwardly from the second lateral edge toward the center of the top panel, and wherein the first and second stress relieving slits of the top panel are aligned with one another along the length of the top panel. In one embodiment, the outer ends of the stress relieving slits adjacent the lateral edges of the top panel are rounded or curved to optimize pouch smoothness when the folder is inserted into the pouch. The embodiment also protects the pouch from potential harm from an otherwise pointed, loaded, folded geometry.

In one embodiment, when the top panel is folded over the bottom panel, the first stress relieving slit of the top panel is aligned with the first stress relieving slit of the bottom panel and the second stress relieving slit of the top panel is aligned with the second stress relieving slit of the bottom panel.

In one embodiment, the package includes a medical device (e.g., a three-dimensional medical device having a length, a width, and a thickness) secured to the folder, whereby the medical device has a section that defines the thickest portion of the medical device, and whereby the stress relieving slits on the top and bottom panels are aligned with the thickest portion of the medical device.

In one embodiment, a device packaging assembly includes a generally rectangular pouch that is sealed on at least three sides. A medical device is supported on a contoured folder made of a substantially flat material. In one embodiment, the folder is made of a material that is resistant to tears. In one embodiment, the folder is moisture absorbing or hydrophobic and is sized to snuggly fit into the pouch on at least three sides. In one embodiment, the term "snug fit" is defined as being a distance that is less than 5 millimeters between the outer perimeter of the device-loaded folder and the inner edges of the seal on the inside of the pouch.

In one embodiment, after the folder is inserted into the pouch, the fourth side of the pouch is sealed adjacent to or near a trailing end of the folder. The fourth sealed side of the pouch is folded to form a pouch fold having a fold line that is immediately adjacent to or abuts against the trailing edge of the device-loaded folder. The pouch fold can be rounded or pinched.

In one embodiment, the contoured folder is further contoured by having at least one stress relieving slit. In one embodiment, the at least one stress relieving slit is preferably adjacent the greatest thickness of the medical device secured on the folder. In one embodiment, the at least one stress relieving slit starts from an aperture near the center of the folder and ends at the periphery of the folder. In one embodiment, the aperture has a diameter that is smaller than the width of the pressure relieving slit. In one embodiment, the opposing walls of the slit have an elliptical or ovoid shape. In one embodiment, the stress relieving slit defines a gap in the folder having a width of about 1-5 millimeters. In one embodiment, the outer ends of the stress relieving slits at the periphery of the folder have rounded or curved surfaces for optimizing pouch smoothness. The embodiment also protects the pouch from potential harm from an otherwise pointed, loaded, folded geometry.

In one embodiment, a contoured folder has a rotation preventing feature including a raised section on the medical device meeting with a raised section on the folder.

In one embodiment, a semi-flexible foil laminate packing system utilizes a two sided smoothing folder to house and secure a medical device in a foil laminate pouch. The semi-flexible foil laminate packaging system preferably includes folding the sealed pouch over a well-seated device-loaded folder to secure the packaging system.

In addition to smoothing the pouch to minimize any potential soft spots that can be more susceptible to external damage, hard folds and wrinkles that may be incurred during the life of the package, the smoothing folder in the folded foil laminate pouch supports the pouch internally to further protect the package from external damage, hard folds and wrinkles.

In one embodiment, a sales unit carton for medical devices may include a foam insert. In one embodiment, the foam insert preferably includes a low-density polyethylene foam (LDPE) insert (e.g., 1.7# density). In one embodiment, the foam insert includes a center cutout or an elongated window formed therein. The center cutout functions as a cushioning element to minimize the effects of hard drop impact forces against the pouch (e.g., at the apex of a chevron shaped seal and chevron shaped leading edges of the top and bottom panels of the folder) for maintaining the integrity of the sealed package. In addition, the cutout in the foam insert also allows for visual inspection to confirm that the pouches loaded into a sales unit carton are loaded in their correct orientation. In one embodiment, the sales unit carton that receives the sealed pouches is sized so as to minimize pouch movement. In one embodiment, the pouch opening flange of the pouch is smoothly rolled a small amount to fit into the sales unit carton with the protective foam insert. The foam insert for the carton further protects the above described packaging system from drop impacts and drop related damages.

In one embodiment, a smoothing folder is disposed within a sealed pouch and fills the inside of the pouch for preventing wrinkling (e.g., when the foil collapses inwardly around the sides of a medical device contained within the package).

These and other preferred embodiments of a package for a medical device will be described in more detail below.

DETAILED DESCRIPTION OF PREFERRED EMBODIMENTS

Figure 1:
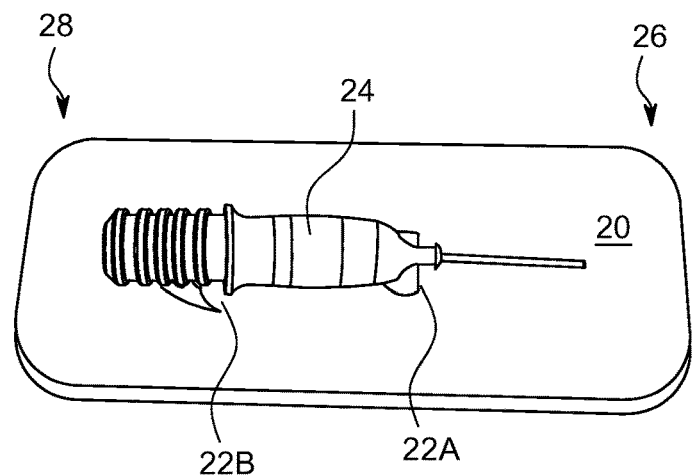
FIG. 1 shows a medical device supported on a card.
Figure 2A:
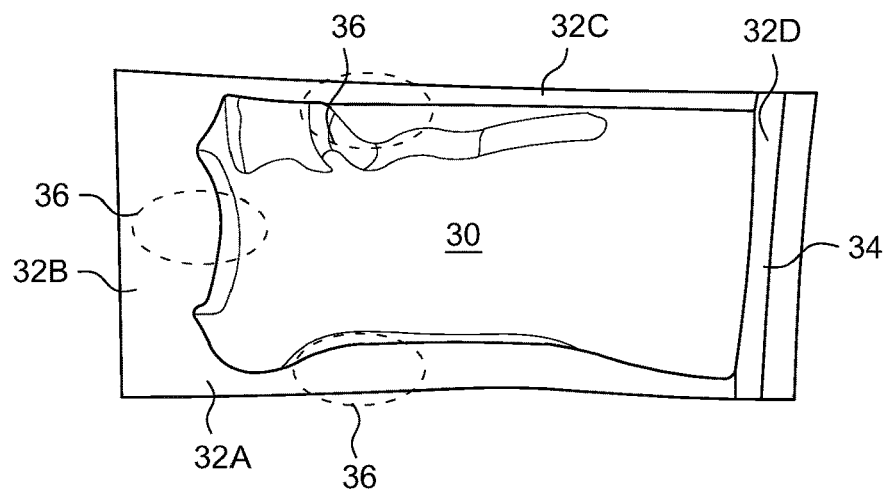
FIGS. 2A and 2B show a pouch containing the medical device and the card shown in FIG. 1.
Figure 2B:
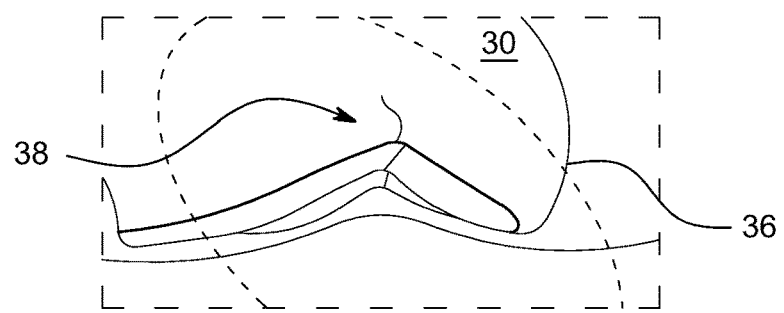
Figure 3A:
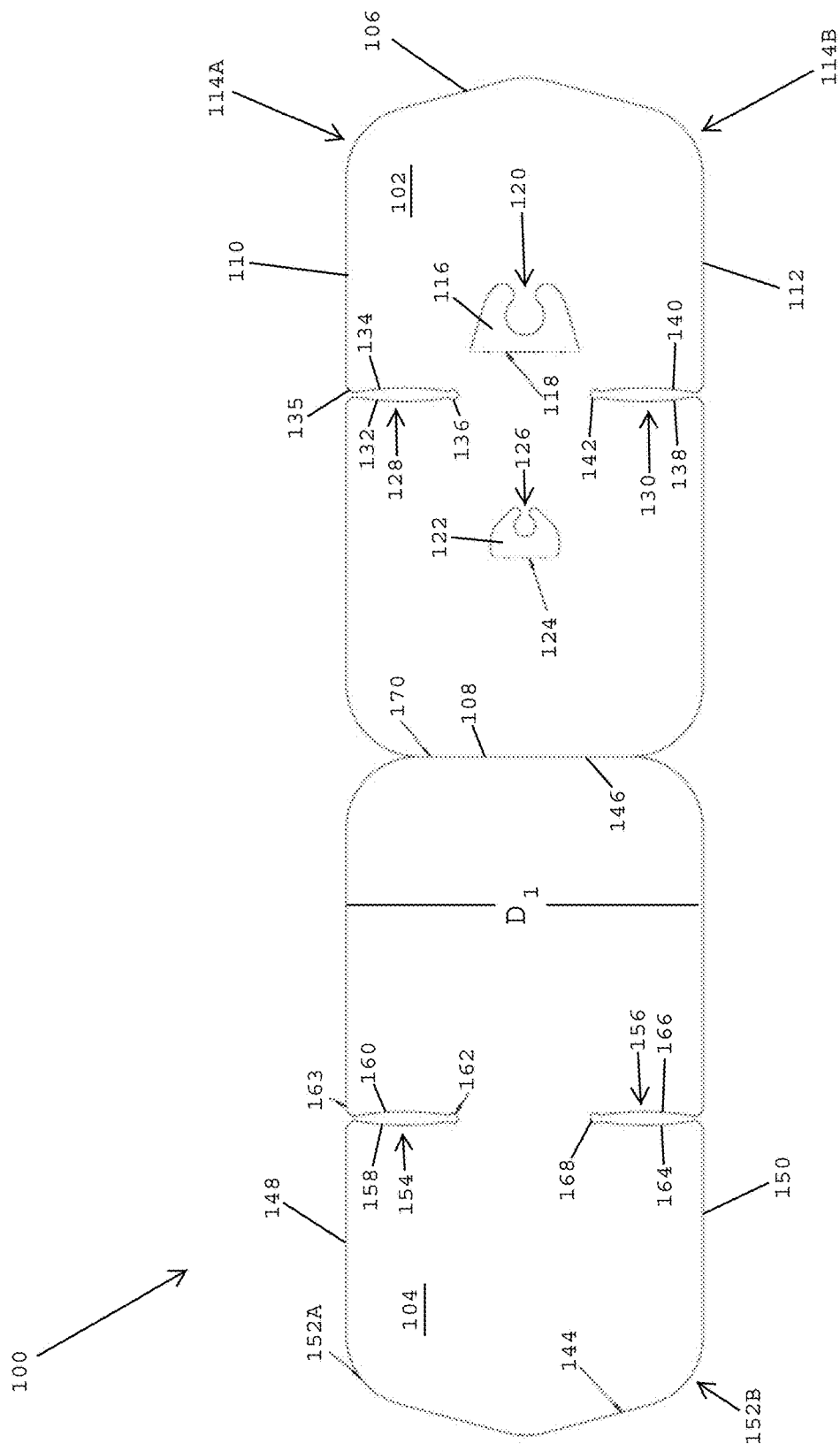
FIGS. 3A and 3B show a folder for securing a medical device, in accordance with one embodiment of the present invention.

Referring to FIG. 3A, in one embodiment, a folder 100 for receiving a medical device includes a bottom panel 102 and a top panel 104 that is designed to fold over the bottom panel 102. The folder 100 is preferably made of a durable inert material such as high density polyethylene (HDPE). In one embodiment, each of the bottom and top panels 102, 104 of the folder 100 has a thickness of approximately 25 mils.

In one embodiment, the bottom panel 102 of the folder 100 includes a leading edge 106, a trailing edge 108 and first and second lateral edges 110, 112 that extend between the leading edge 106 and the trailing edge 108. In one embodiment, the leading edge 106 of the bottom panel 102 has an angled, chevron shape with an apex that matches the angled, chevron shape of a seal found at a sealed end of a pouch. In one embodiment, the corners 114A, 114B of the leading edge 106 of the bottom panel 102 are rounded where the leading edge 106 meets the first and second lateral side edges 110, 112.

In one embodiment, the bottom panel 102 includes a first medical device securing element 116 having a base that is flexibly secured to the bottom panel 102 via a fold line 118 so that the first medical device securing element 116 may be folded flat relative to the top surface of the bottom panel 102, or erected into an upright configuration to extend away from the top surface of the bottom panel 102. In one embodiment, the first medical device securing element 116 includes an opening 120 that is adapted to receive a section of a medical device (e.g., a plunger section) for securing the medical device atop the bottom panel 102 of the folder 100.

In one embodiment, the bottom panel 102 of the folder 100 includes a second medical device securing element 122 having a base that is flexibly secured to the bottom panel 102 via a fold line 124. The second medical device securing element 122 may be folded flat relative to the top surface of the bottom panel 102 or may be erected to extend away from the top surface of the bottom panel 102 for supporting a second section of a medical device (e.g., a dispensing catheter). The second medical device securing element 122 includes an opening 126 that is adapted to receive and seat a portion of a medical device secured atop the bottom panel 102 of the folder 100.

In one embodiment, the bottom panel 102 of the folder 100 includes a first stress relieving slit 128 that extends inwardly from the first lateral edge 110, and a second stress relieving slit 130 that extends inwardly from the second lateral edge 112. In one embodiment, the first and second stress relieving slits 128, 130 are aligned with one another along the long axis of the bottom panel 102. In one embodiment, the first and second stress relieving slits are located between the first and second medical device securing elements 116, 122. In one embodiment, when a three-dimensional medical device is secured atop the bottom panel 102, the first and second stress relieving slits are aligned with the thickest section of a medical device secured atop the bottom panel 102 of the folder 100. In one embodiment, the outer ends of the stress relieving slits have a curved or rounded surface 135 adjacent the lateral edges 110, 112 of the bottom panel 102.

In one embodiment, the opposing laterally extending walls 132, 134 of the first stress relieving slit 128 have an ovoid or elliptical shape, and the inner most end of the first stress relieving slit 128 has a rounded apex 136. In one embodiment, the rounded apex 136 has a diameter that is less than the width of the first stress relieving slit 128. Although the present invention is not limited by any particular theory of operation, it is believed that providing a first stress relieving slit 128 having opposing elliptical shaped walls 132, 134, a rounded apex 136 at the inner most end of the stress relieving slit, and rounded or curved outer ends 135 will provide better smoothing capabilities for a sealable pouch and eliminate or minimize the likelihood of any sharp edges on the folder 100 contacting the walls of the pouch.

In one embodiment, the second stress relieving slit 130 has opposing side walls 138, 140 having an elliptical or ovoid shape and a rounded apex 142 at the inner most end of the second stress relieving slit. In one embodiment, the rounded apex 142 has a diameter that is less than the width of the second stress relieving slit 130.

In one embodiment, the top panel 104 of the folder 100 includes a leading edge 144, a trailing edge 146, and first and second lateral sides 148, 150 that extend between the leading edge 144 and the trailing edge 146. In one embodiment, the leading edge 144 has an angled, chevron shape with an apex that matches the angled chevron shape of the leading edge 106 of the bottom panel 102 of the folder 100, as well as the angled, chevron shape of the sealed end of a sealable pouch, as will be described in more detail herein. In one embodiment, the leading edge 144 of the top panel 104 includes rounded corners 152A, 152B that extend between the leading edge 144 and the first and second lateral edges 148, 150 of the top panel.

In one embodiment, the top panel 104 of the folder 100 includes a first stress relieving slit 154 that extends inwardly from the first lateral edge 184, and a second stress relieving slit 156 that extends inwardly from the second lateral edge 150. In one embodiment, the first stress relieving slit 154 has opposing first and second walls 158, 160 having an ovoid or elliptical shape. In one embodiment, a rounded apex 162 defines an inner-most end of the first stress relieving slit 154.

In one embodiment, the second stress relieving slit 156 of the bottom panel 104 includes opposing side walls 164, 166 having an ovoid or elliptical shape and a rounded apex 168 at an inner-most end of the second stress relieving slit 156. In one embodiment, the first and second stress relieving slits 154, 156 of the top panel are aligned with one another along the length of the top panel 104 of the folder 100. In one embodiment, the outer ends of the stress relieving slits of the top panel have rounded or curved surfaces 163.

In one embodiment, the trailing edge 108 of the bottom panel 102 of the folder 100 and the trailing edge 146 of the top panel 104 of the folder 100 are joined together along a foldable score line 170, which enables the top panel 104 to be folded over the bottom panel 102. In one embodiment, when the top panel 104 is folded over the bottom panel 102, the first stress relieving slit 154 on the top panel 104 is aligned with the first stress relieving slit 128 on the bottom panel 102, and the second stress relieving slit 156 on the top panel 104 is aligned with the second stress relieving slit 130 on the bottom panel 102. In one embodiment, the stress relieving slits are aligned with the thickest section of a three-dimensional medical device that is secured to the bottom panel 102 of the folder 100. In one embodiment, the stress relieving slits have an elliptical or ovoid shape and terminate at rounded apexes having diameters that are less than the thicknesses of the slits associated therewith.

Figure 3B:
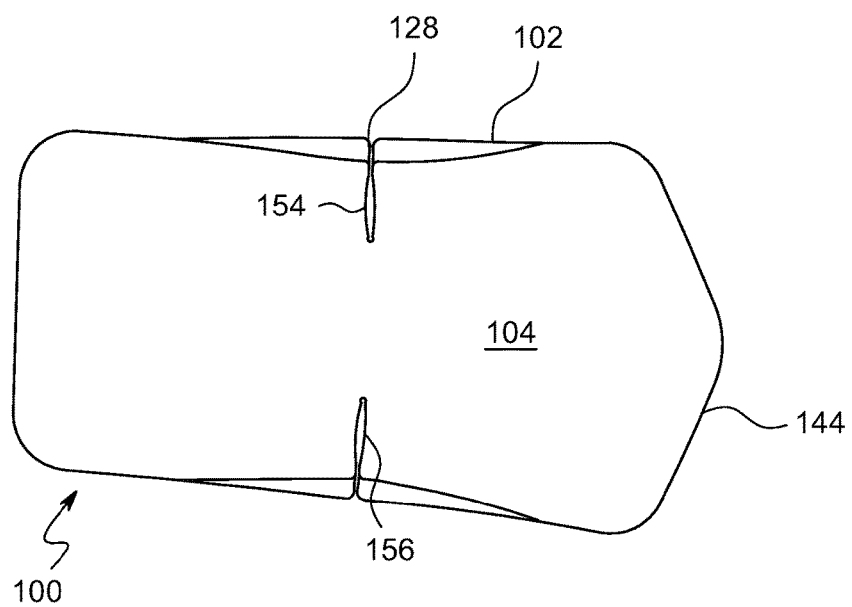

Referring to FIGS. 3A and 3B, in one embodiment, a medical device is positioned atop the bottom panel 102 of the folder 100 and secured to the bottom panel using the first and second medical device securing elements 116, 122. In one embodiment, the top panel 104 is folded over the bottom panel 102 at the fold line 170 so that the chevron-shaped leading edge 144 of the top panel 104 is aligned with the chevron-shaped leading edge 106 of the bottom panel 102. In addition, the first stress relieving slit 154 of the top panel 104 is aligned with the first stress relieving slit 128 of the bottom panel 102, and the second stress relieving slit 156 of the top panel 104 is aligned with the second stress relieving slit 130 of the bottom panel 102. The medical device is preferably disposed between the opposing inner faces of the top and bottom panels.

In one embodiment, the folder is constructed of a high-density polyethylene material (HDPE) or similar inert and durable material. The folder may be customized for each particular medical device and each particular foil laminate pouch. In one embodiment, the folder is preferably made of a hydrophilic material. In one embodiment, the folder is made of cellulose material such as paper or paperboard. The folder may act as a desiccant material for removing excess moisture from inside a sealed package or from a medical device stored in the sealed package.

Figure 4:
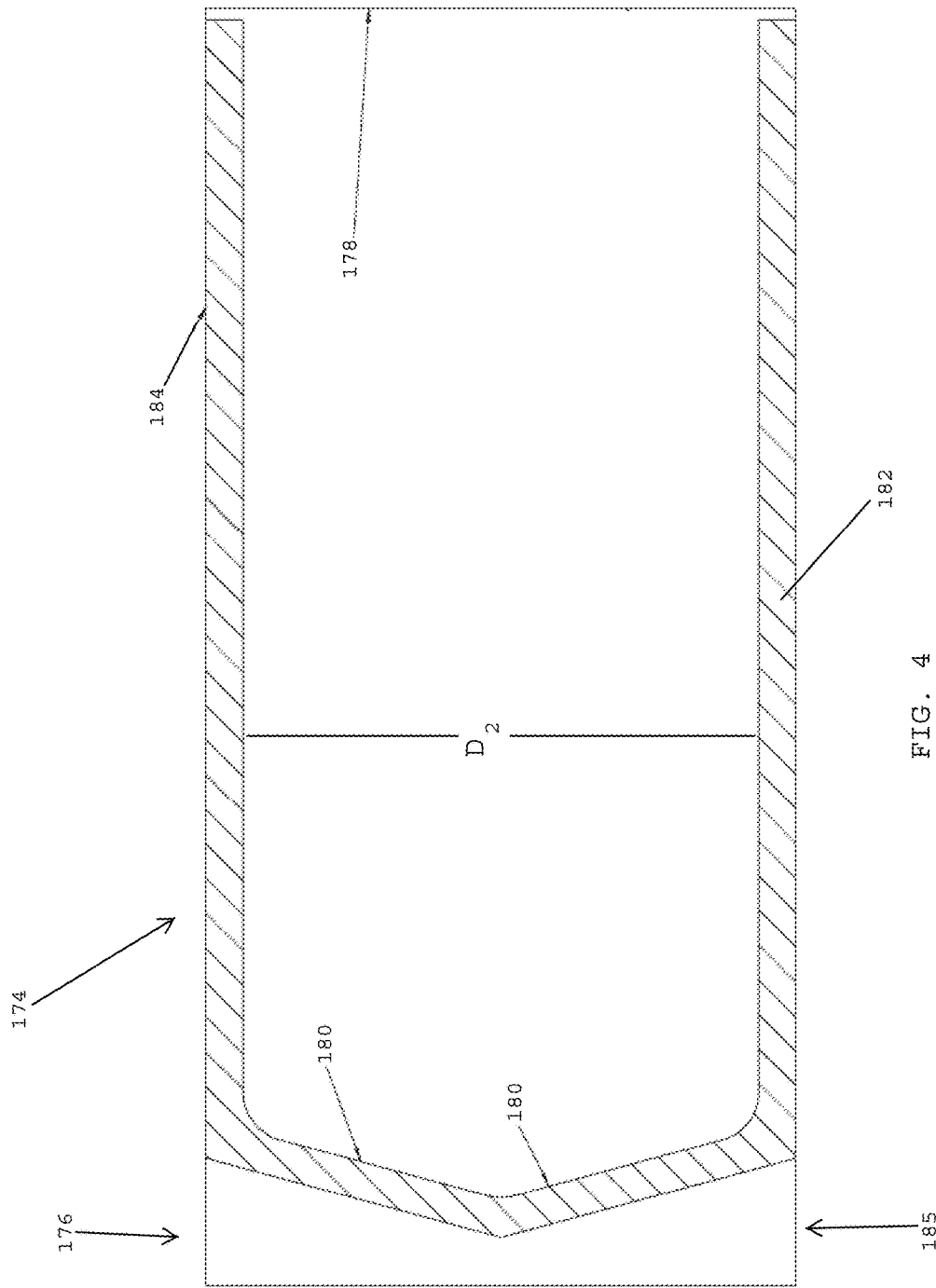
FIG. 4 shows a sealable pouch that receives the folder shown in FIGS. 3A and 3B, in accordance with one embodiment of the present invention.

Referring to FIG. 4, in one embodiment, the folder 100 shown and described above in FIGS. 3A and 3B is insertable into a sealable pouch 174 having a closed end 176 and an open end 178. In one embodiment, the sealable pouch may be a foil laminate pouch including foil and polyester and/or foil and nylon. In one embodiment, the sealable pouch 174 is a foil pouch that is initially sealed along three sides including a chevron shaped seal 180 adjacent the closed end 176 of the pouch 174 and first and second lateral side seals 182, 184 that extend along the side edges of the pouch 174. In one embodiment, the chevron shaped seal 180 has a shape and configuration that matches the chevron shapes of the leading edges 106, 144 of the bottom and top panels 102, 104 of the folder 100 (FIG. 3A). In one embodiment, the first and second lateral side seals 182, 184 extend from the outer ends of the chevron shape seal 180 toward the open end 178 of the foil patch 174. In one embodiment, the pouch 174 includes two layers of material that are joined together by the chevron shaped seal 180 and the first and second lateral seals 182, 184. In one embodiment, the leading edges of the top and bottom panels and the seal 180 may have different geometric shapes that match one another (e.g., curved, straight).

In one embodiment, a foil laminate pouch for a medical device preferably includes first and second flexible sheets having opposing inner surfaces joined together by one or more seals for defining a sealed area of the pouch located inside the seal and an unsealed area of the pouch located outside the seal. The pouch preferably has an opening flange located adjacent an edge of the pouch for peeling the first and second sheets away from one another for breaking the seal and opening the sealed pouch for removing the contents therein. In one embodiment, the opening flange is desirably located within the unsealed area of the pouch.

In one embodiment, a folder containing a medical device is preferably disposed within the sealed area of a pouch. The sealed area is preferably sterile for maintaining the folder and the medical device in a sterile state. The folder and the medical device are desirably removable from the pouch by peeling first and second sheets of the pouch away from one another for breaking the seal and opening the sealed pouch.

In one embodiment, the pouches may be made from sheets of continuous roll stock. The sheets of continuous roll stock may be feed downstream by a conveyor system to a sealing station at which the sheets are sealed to define a plurality of separate pouches. The plurality of pouches may be cut from the roll stock to provide a plurality of separate pouches. The order of steps for sealing and cutting may be modified as necessary. In one embodiment, the roll stock may be first sealed, and then cut into separate pouches. In one embodiment, the pouches are first cut into separate pouches and then sealed. The above steps may be performed by a pouch manufacturer to provide a plurality of sealed pouches, with each pouch having a pouch opening adapted to receive a folder containing a medical device.

In one embodiment, a seal preferably extends adjacent a first lateral side, a second lateral side, and a leading edge of the pouch. Initially, the trailing edge of the pouch remains unsealed. The seal may be formed using adhesive, heat, energy or pressure, or combinations thereof. In one embodiment, the seal desirably includes a first leg that extends adjacent the leading edge of the pouch, a second leg that extends adjacent the first lateral edge of the pouch, and a third leg that extends adjacent the second lateral edge of the pouch. In one embodiment, the first leg at the leading edge has a chevron shape with an apex that divides the first leg into a first section and a second section. In one embodiment, the first and second sections of the chevron-shaped first leg of the seal are preferably angled relative to one another. In one embodiment, the first section of the first leg defines an angle of about 10-20° and more preferably about 15° with the leading edge of the pouch. The second section of the first leg defines an angle of similar scope with the leading edge of the pouch. In one embodiment, the seal has a width of about 5-10 mm. In one embodiment, the first leg of the seal at the leading edge may have different geometric shapes including curves and straight edges that match the shapes of the leading edges of the folder.

When folded, the folder 100 (FIG. 3A) is desirably inserted into the opening 178 (i.e., unsealed end) of the foil patch 174 prior to the open end 178 of the pouch being sealed so that the folder and the medical device contained on the folder are hermetically sealed inside the pouch 174. In one embodiment, the pouch 174 includes a pouch opening flange 185 located outside the sealed area of the pouch that enables the two joined layers of material to be pulled apart for breaking the seal and accessing the folder inside the pouch.

Referring to FIGS. 3A and 4, in one embodiment, the lateral distance between the first and second sides of the bottom panel 102 and the top panel 104 of the folder is designated $D_1$, and this distance substantially matches the distance $D_2$ between the first and second lateral seals 182, 184. As a result, once the folder 104 has been inserted into the open end 178 of the pouch, the folder 104 will not shift laterally within the pouch 174. In one embodiment, the chevron shaped leading ends of the top and bottom panels 102, 104 of the folder 100 abut against the inside of the chevron shaped seal 180 at the closed end 176 of the pouch 174. After the folder 100 has been fully inserted into the pouch 174, the open end 178 is preferably sealed by forming a fourth seal (not shown) that extends from the first lateral seal 182 to the second lateral seal 184.

Figure 5A:
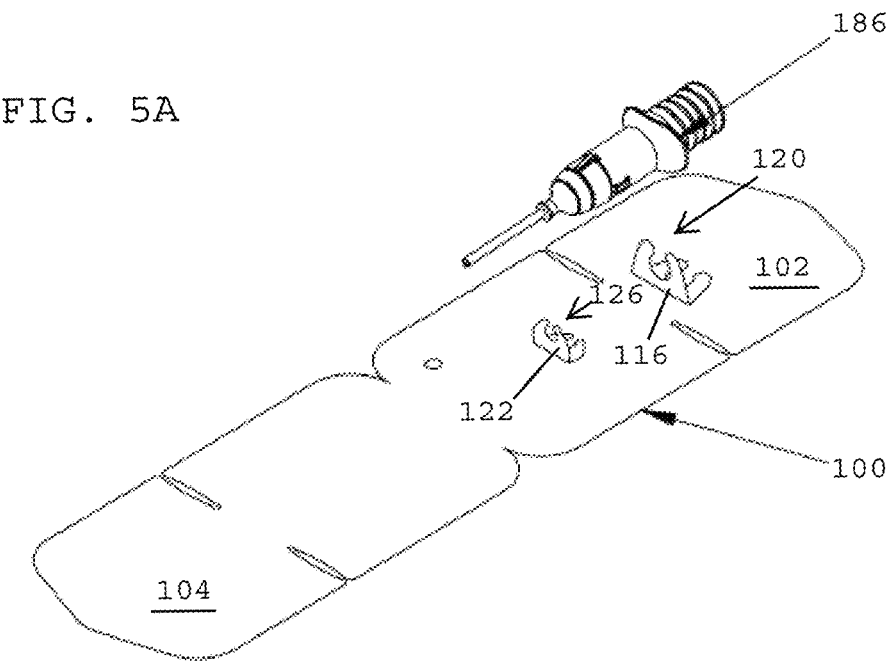
FIGS. 5A-5G show a method of securing a medical device on a folder and sealing the resulting subassembly inside a sealable pouch, in accordance with one embodiment of the present patent application.

Referring to FIG. 5A, in one embodiment, a folder 100 is laid flat so that the bottom panel 102 and the top panel 104 lie in a common plane. A medical device 186 is juxtaposed with the top surface of the bottom panel 102.

Figure 5B:
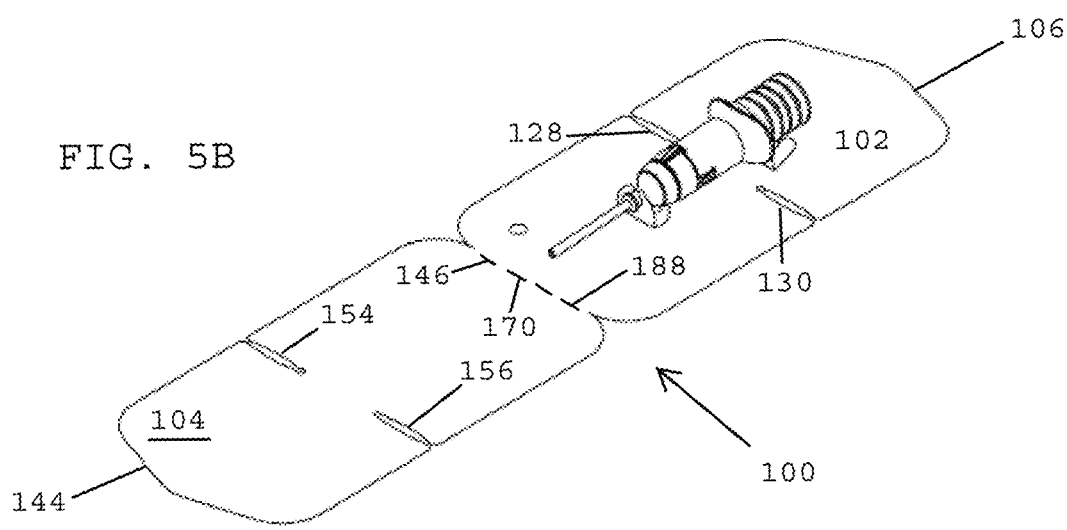

Referring to FIGS. 5A and 5B, in one embodiment, the first and second medical device securing elements 116, 122 are erected into an upright configuration so that the respective openings 120, 126 of the first and second medical device securing elements oppose an underside of the medical device 186. Referring to FIG. 5B, sections of the medical device 186 are pressed into the openings 120, 126 of the first and second medical device securing elements 116, 122 for securing the medical device to the bottom panel 102 of the folder 100.

Figure 5C:
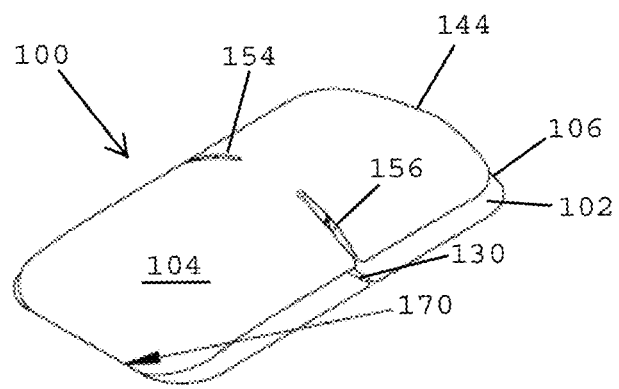

Referring to FIGS. 5B and 5C, in one embodiment, the top panel 104 of the folder 100 is folded over the bottom panel 102 of the folder 100 so that the top or inner surface of the top panel 104 covers the medical device 186 and opposes the top or inner surface of the bottom panel 102. In one embodiment, the top panel 104 and the bottom panel 102 are folded along the fold line 170 that interconnects the trailing end 108 of the bottom panel and the trailing end 146 of the top panel. Referring to FIG. 5C, after the top panel 104 has been folded over the bottom panel 102, the leading edges 144, 106 of the respective top and bottom panels are aligned with one another. In addition, the first stress relieving slit 154 of the top panel 104 is aligned with the first stress relieving slit 128 of the bottom panel 102, and the second stress relieving slit 156 of the top panel 104 is aligned with the second stress relieving slit 130 of the bottom panel 102.

Figure 5D:
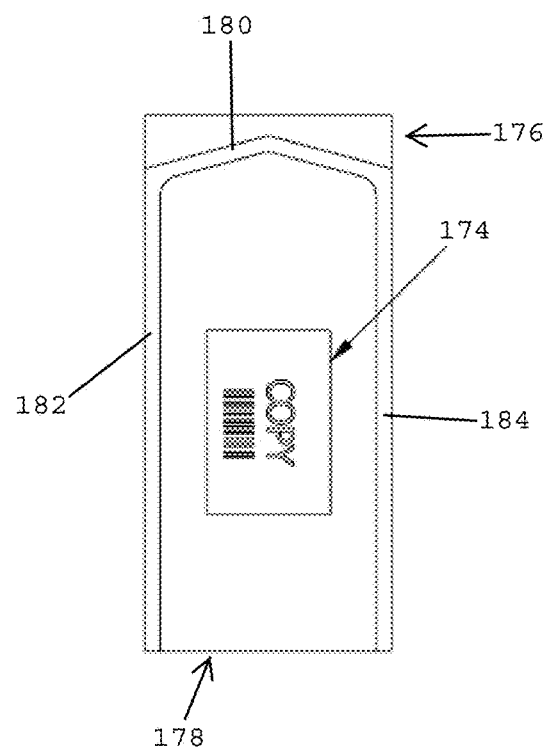

Referring to FIG. 5D, in one embodiment, the folder carrying the medical device is designed to be inserted into the pouch 174 having the closed end 176 and the open end 178 into which the leading edges of the folder are inserted. The pouch includes three seals with the chevron shaped seal 180 adjacent to closed end 176 and first and second lateral side seals 182, 184 extending from the outer ends of the chevron shaped seal 180 toward the open end 178 of the pouch 174.

Figure 5E:
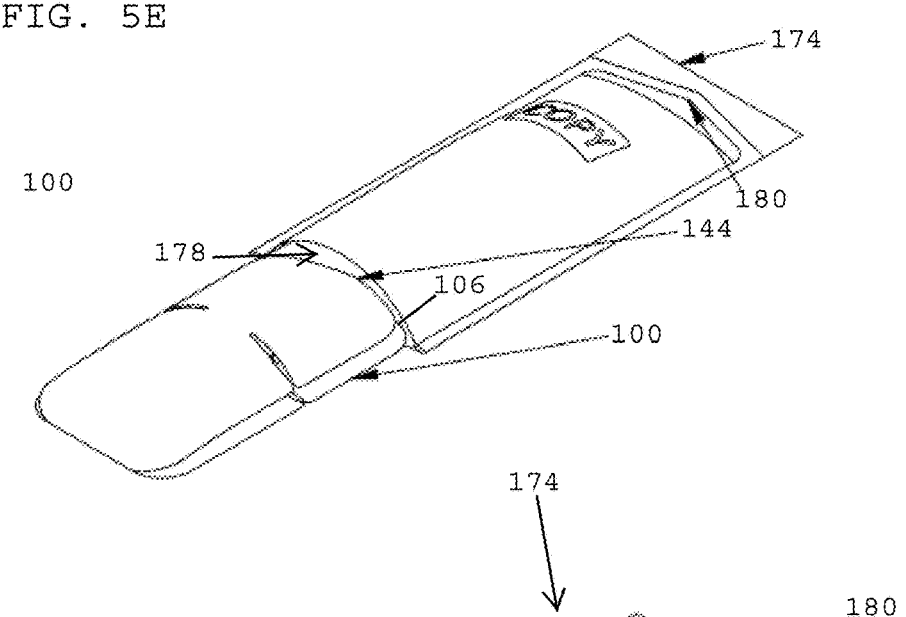

Referring to FIG. 5E, in one embodiment, with the folder 100 in the folded configuration, the chevron shaped leading edges 144, 106 of the top and bottom panels of the folder are juxtaposed with the open end 178 of the pouch 174. The chevron shaped leading edges 144, 106 are advanced toward the chevron shaped seal 180 of the pouch 174 until the chevron shaped leading edges 144, 106 touch the chevron shaped seal 180.

Figure 5F:
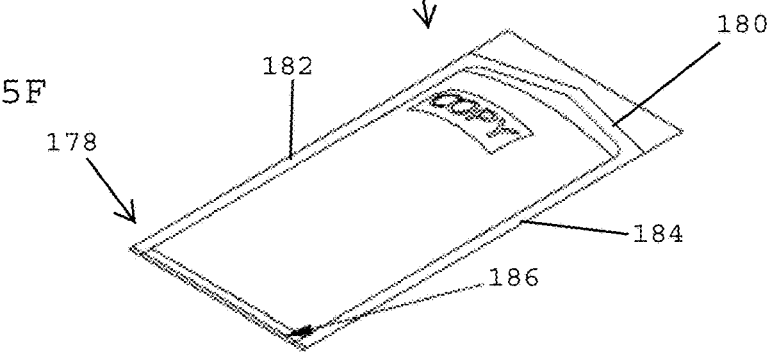

Referring to FIG. 5F, after the folder has been fully inserted inside the pouch 174, a fourth seal 186 is formed at the open end 178 of the pouch 174. In one embodiment, the fourth seal 186 extends between the first and second side seals 182, 184 for completely sealing the folder 100 and the medical device within the pouch 174.

Figure 5G:
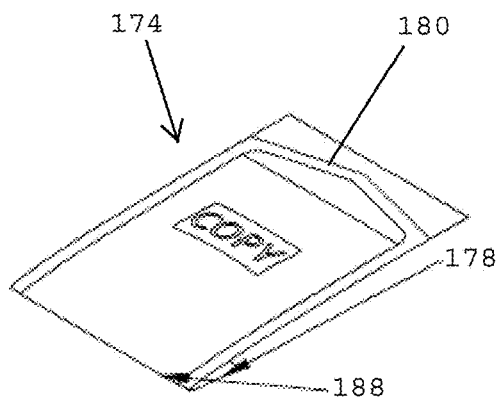

Referring to FIGS. 5F and 5G, in one embodiment, the folder is fully seated inside the pouch 174 so that the chevron shaped leading edges of the folded folder abut against the chevron shaped seal 180 of the pouch. The sealed end 178 of the pouch that contains the fourth seal 186 is folded around the trailing edges of the top and bottom panels of the folder. In one embodiment, the sealed end 178 is folded so that it lies under the bottom panel of the folder. In one embodiment, as the fourth sealed end 178 of the pouch 174 is folded over a trailing edge of the folder, care is taken to not pinch the pouch along the folding line. In one embodiment, the folding line 188 is positioned close to or abutting against the trailing edges of the top and bottom panels of the folder contained within the sealed pouch 174.

Figure 6A:
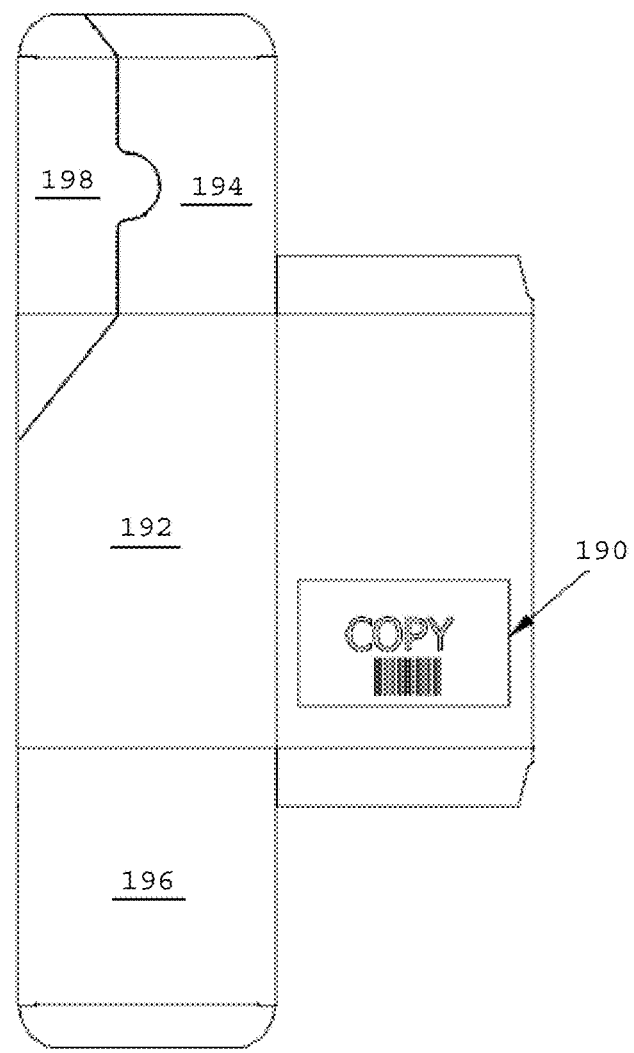
FIGS. 6A-6H show a method of packing the sealed pouch of FIG. 5G into a carton, in accordance with one embodiment of the present invention.

Referring to FIG. 6A, in one embodiment, a carton 190, such as a sales unit carton, is utilized for storing the sealed pouches 174 (see FIG. 5G). The sales unit carton 190 includes a main body 192 having a box-like shape, a front closing flap 194, and a back closing flap 196. The front closing flap 194 and a leading edge of the main body 192 include a removable, tear away panel 198 that may be removed for providing access to the front of the carton 190 and the sealed pouches loaded into the carton, as will be described in more detail herein.

Figure 6B:
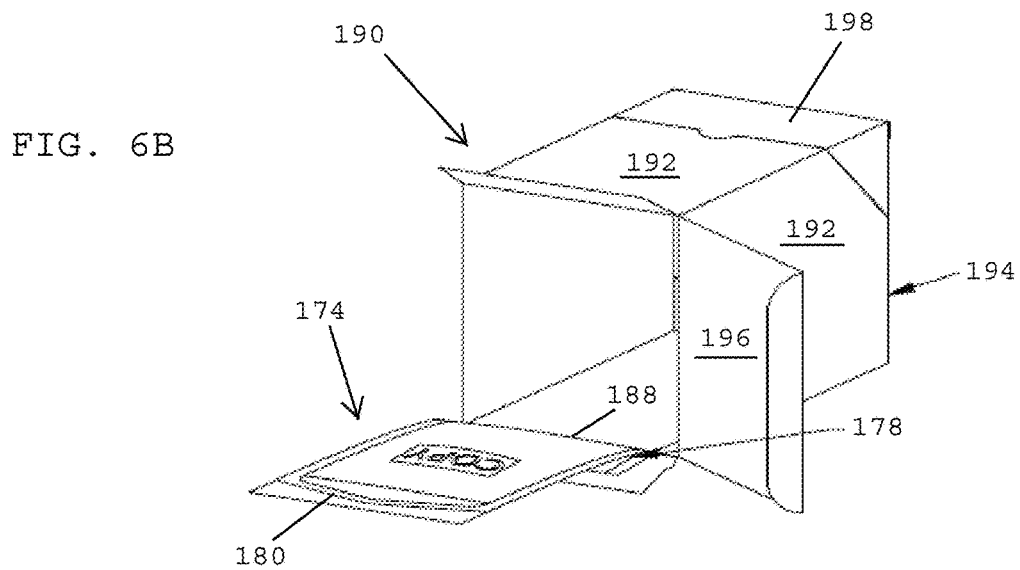

Referring to FIG. 6B, in one embodiment, the sales unit carton 190 is assembled so that the main body 192 has a box-like shape with the front side of the main body 192 covered by the front flap 194 and the removable, tear away panel 198. The rear flap 196 covering the trailing end of the main body 192 is opened so that the sealed pouch packages 174 may be inserted into the carton 190.

In one embodiment, as shown in FIG. 6B, the folded end 178 of each sealed pouch 174 is juxtaposed with the opening to the main body 192 at the trailing end of the carton 190. The folded end 178 of the sealed pouch is inserted into the rear opening and advanced toward the front panel 194 of the carton 190. After being loaded into the carton, the chevron shaped seal 180 of the pouch 174 faces away from the front panel 194 and toward the rear or trailing end of the main body 192.

Figure 6C:
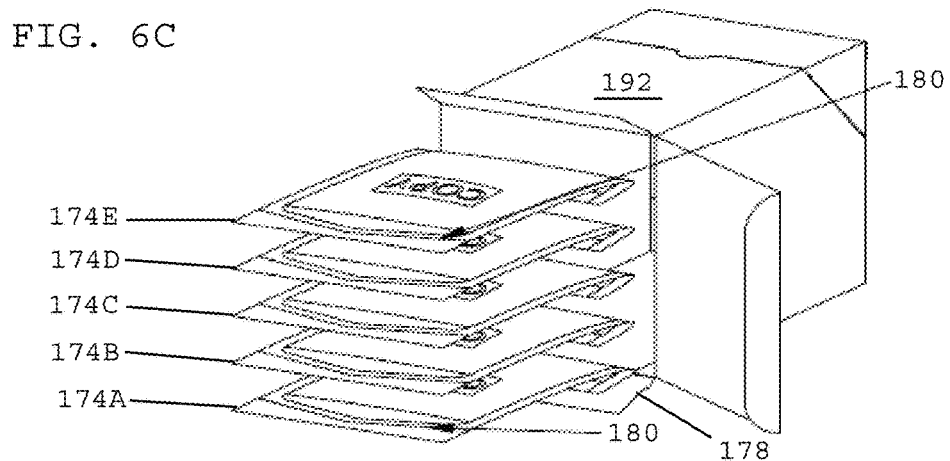

Referring to FIG. 6C, in one embodiment, a set of sealed pouches 174A-174E may be inserted into the opening at the trailing end of the main body 192 of the carton 190. Each sealed pouch 174A-174E is oriented similarly as described above for FIG. 6B so that the folded ends 178 of the respective pouches enter first and the chevron sealed ends 180 face toward the rear or trailing side of the main body.

Figure 6D:
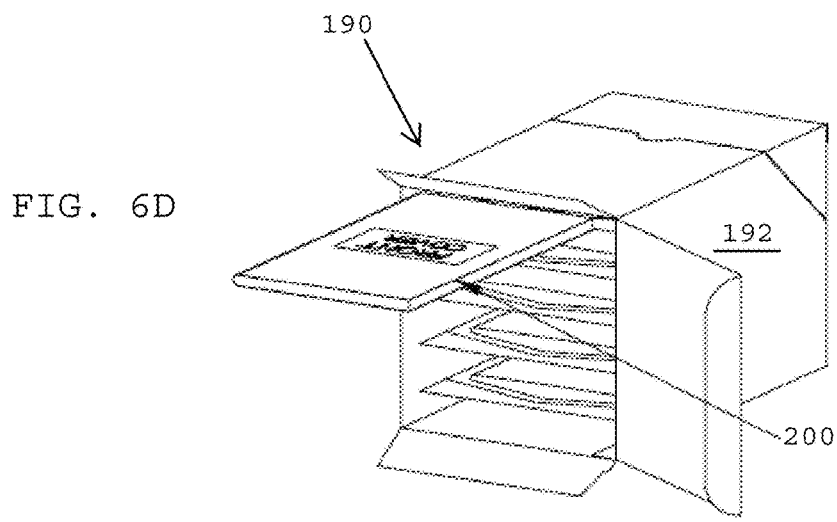

Referring to FIG. 6D, in one embodiment, an instruction for use (IFU) manual 200 may be positioned atop the uppermost sealed foil package that has been loaded into the main body 192 of the sales unit carton 190. FIG. 6D shows an embodiment with five sealed pouches loaded into the sales unit carton 190, however, other embodiments may have fewer or more sealed pouches loaded into a sales unit carton.

Figure 6E:
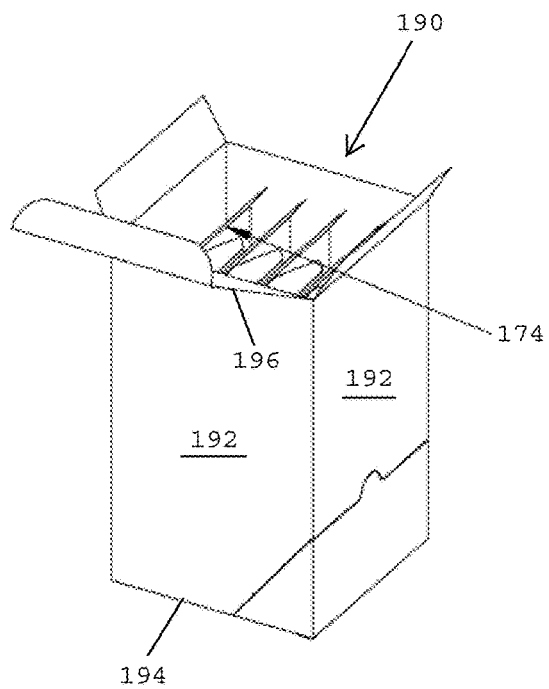

Referring to FIG. 6E, in one embodiment, after the sealed pouches have been loaded into the carton 190, the main body 192 of the carton 190 is rotated so that the rear panel 196 is above the front panel 194 of the main body 192. In one embodiment, the pouch opening flanges 185 of all of the sealed pouches 174 are curled in the same direction.

Figure 6F:
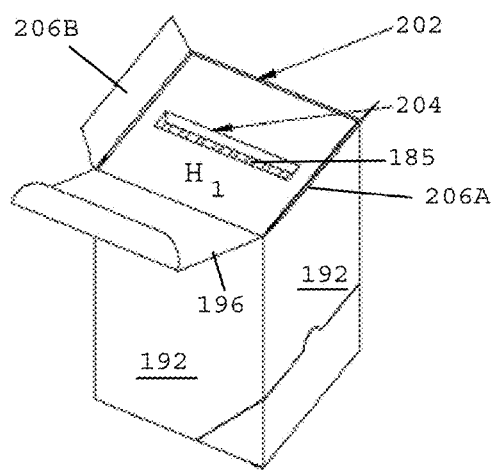

Referring to FIGS. 6E and 6F, in one embodiment, before the rear flap 196 of the sales unit carton 190 is closed, a foam insert 202 is positioned atop the curled opening flanges 185 of the sealed pouches 174. In one embodiment, the foam insert 202 desirably includes a window 204 that extends across the height $H_1$ of the main body 192 of the carton 190. The elongated inspection window 204 serves various functions. A first function is to provide an inspection window to confirm that the pouch opening flanges 185 are uniformly curled in the same direction. A second function is to align the inspection window with the apex of the chevron shaped seal 180 (FIG. 4) of the pouch 174 and the apex of the chevron shaped leading edges 106, 144 of the folder 100 (FIG. 3A), which provides enhanced cushioning for the sealed pouches. The back side of the carton 190 may then be close by folding first and second lateral flaps 206A, 206B over the foam insert 202 and the rear flap 196 over the first and second lateral flaps 206A, 206B.

Figure 6G:
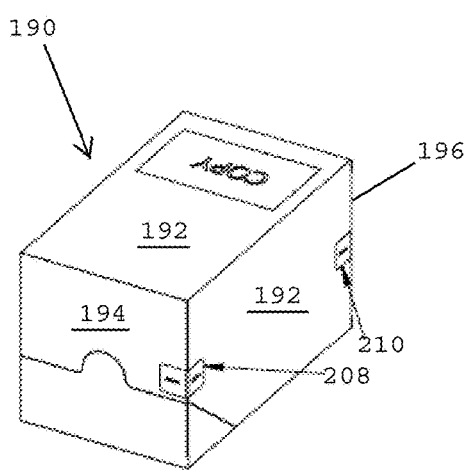

Referring to FIG. 6G, in one embodiment, a first security label 208 may be positioned at a corner edge between the front flap 194 and a leading end of the main body 192. A second security label 210 may be positioned between the rear flap 196 and a trailing end of the main body 192. The first and second security labels 208, 210 provide confirmation that the carton 190 has not been tampered with and/or that an unauthorized opening of the carton 190 has occurred.

Figure 6H:
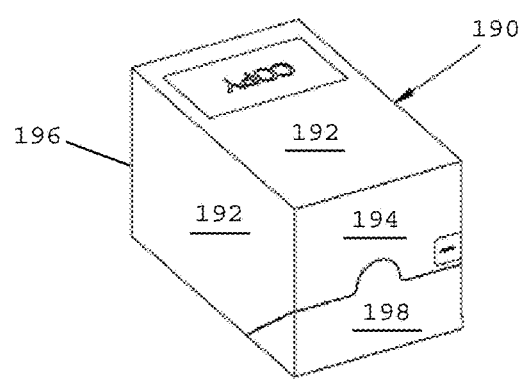

Referring to FIG. 6H, in one embodiment, each packed sales unit carton 190 preferably includes a plurality of the sealed and folded pouches disclose herein, which are stacked atop one another within the carton 190. The folded over sealed ends of the pouch are adjacent the front flap 194 and the chevron shaped sealed ends of the pouches are adjacent the rear flap 196 of the carton 190.

Figure 6I:
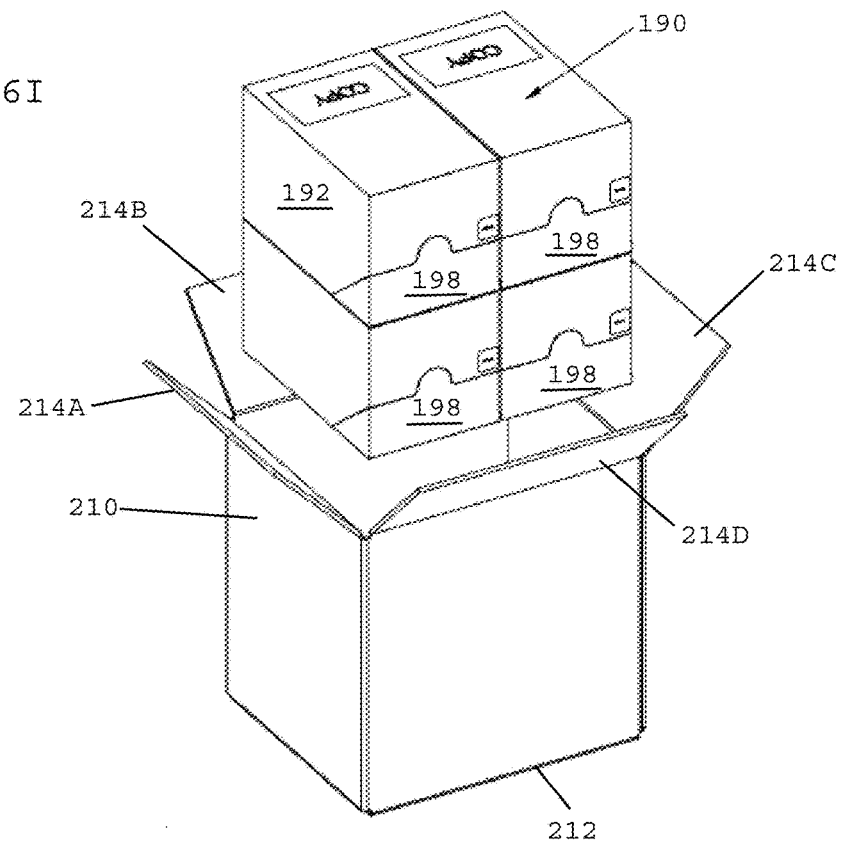
FIGS. 6I and 6J show a method of packing the carton of FIG. 6H into a shipping container, in accordance with one embodiment.

Referring to FIGS. 6H and 6I, in one embodiment, a plurality of the fully assembled cartons 190 may be packed into a shipping container 210 that is designed to hold two or more sales unit cartons 190. In one embodiment, prior to inserting the sales unit cartons 190 into the shipping container 210, the cartons 190 are oriented so that the tear away panels 198 at the fronts of the respective main bodies 192 are oriented toward a closed, bottom end 212 of the shipping container 210.

Figure 6J:
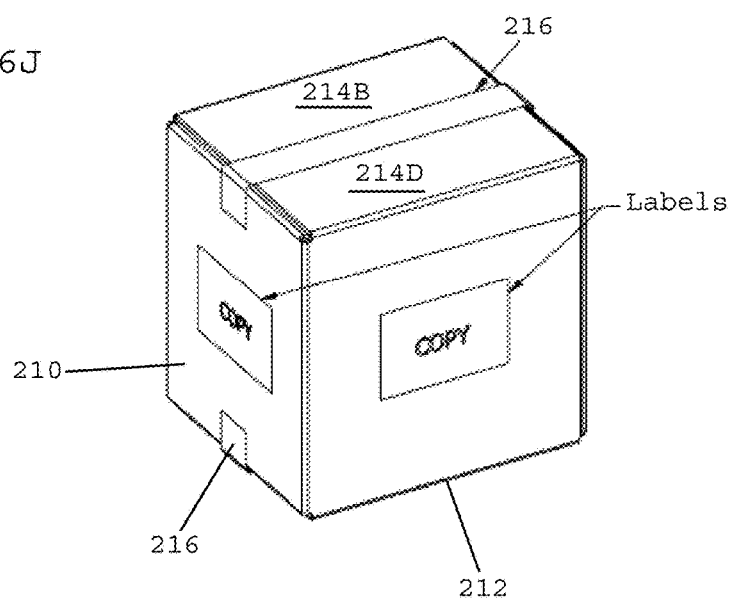

Referring to FIGS. 6I and 6J, in one embodiment, after the cartons 190 have been loaded into the shipping container 210, the top closing flaps 214A-214D of the shipping container may be folded over the open end of the shipping container and held in a closed configuration by shipper tape 216 that extends across the width and sides of the shipping container 210. Shipper tape 216 may also be used to secure the closing panels at the closed end 212 of the shipping container 210.

Figure 7A:
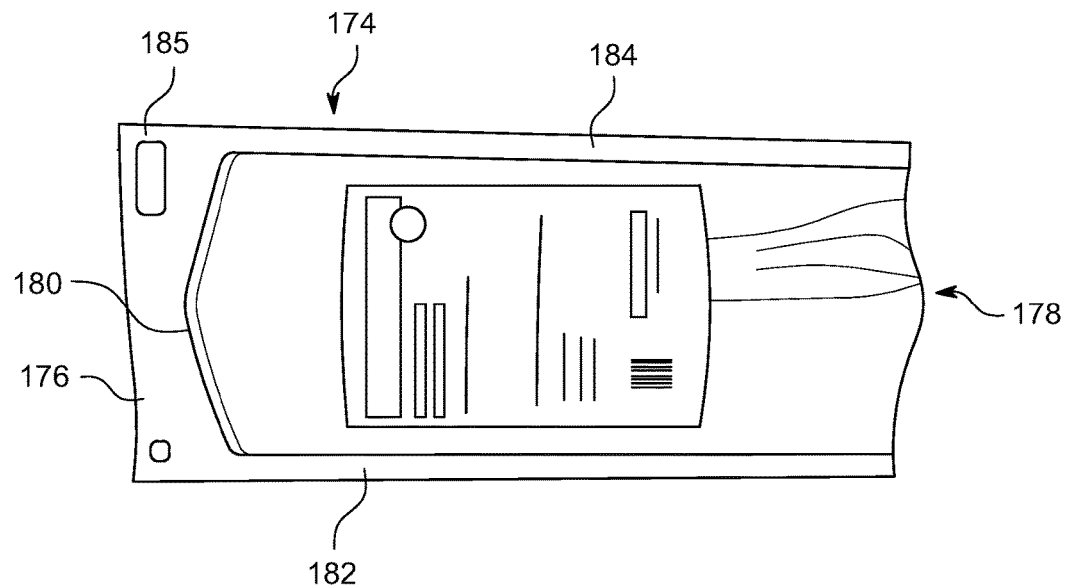
FIGS. 7A-7D show a method of sealing and folding a pouch for a medical device, in accordance with one embodiment.

Referring to FIG. 7A, in one embodiment, a sealable pouch 174 includes a sealed end 176 having a pouch opening flange 185 and an open end 178 that is unsealed and that is adapted to receive a folder 100 (FIG. 3A) containing a medical device. The pouch 174 includes a chevron shaped seal 180 at the sealed end 176, and first and second side seals 182, 184 that extend from the outer ends of the chevron shaped seal 180 to the open end 178 of the pouch 174.

Figure 7B:
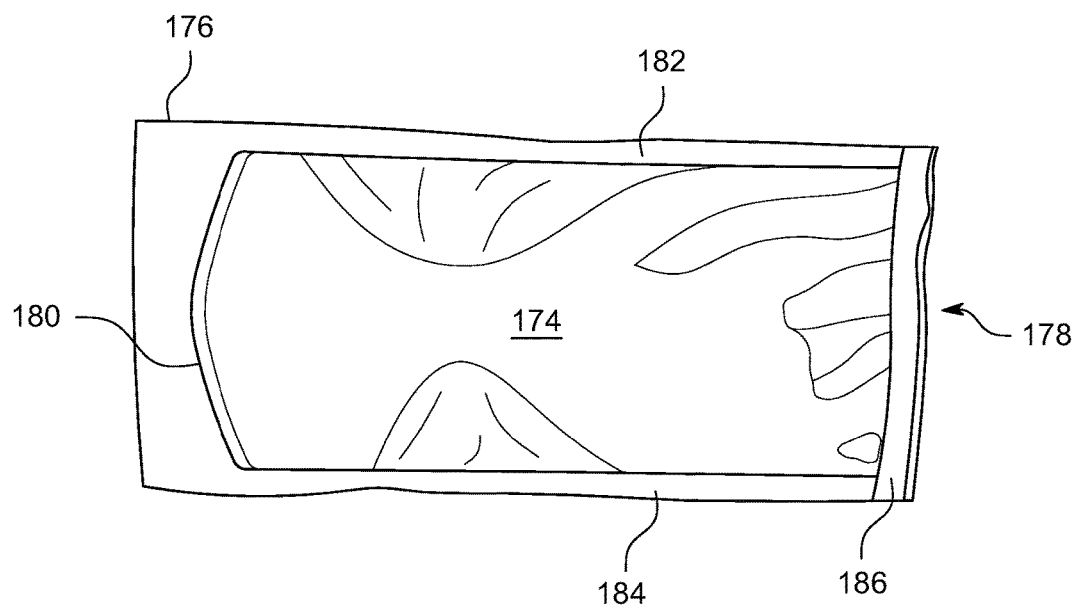

Referring to FIG. 7B, in one embodiment, the leading edges of the folder are inserted into the open end 178 of the pouch 174 and advanced toward the chevron shaped seal 180 at the sealed end 176 of the pouch 174 until the chevron shaped leading edges of the folder abut against the inside of the chevron shaped seal 180. The lateral sides of the folder desirably abut against the first and second lateral seals 182, 184. The open end 178 of the pouch 74 may be sealed using a fourth seal 186 that extends between the first lateral seal 182 and the second lateral seal 184.

Figure 7C:
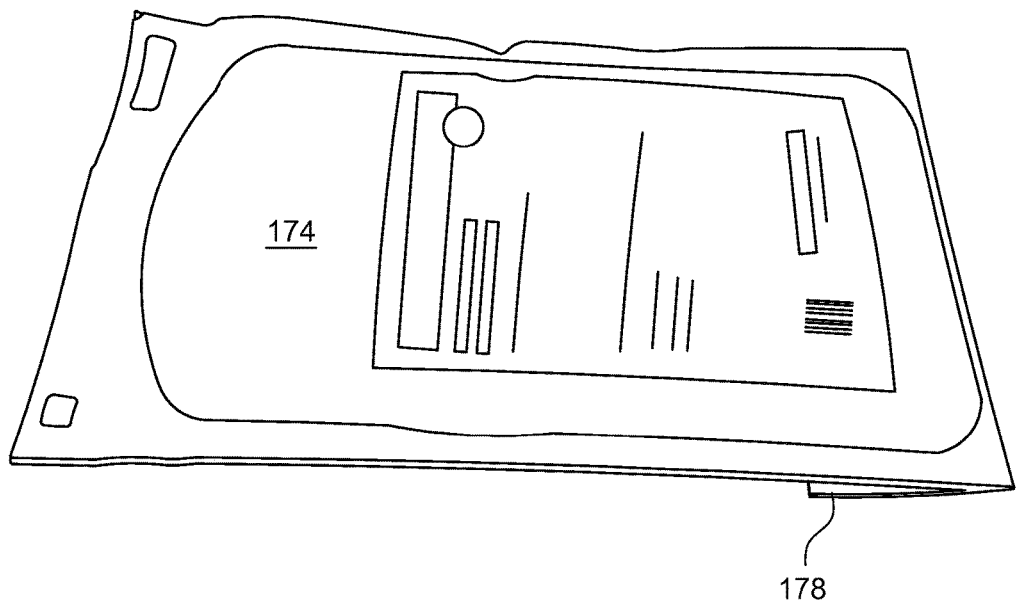
Figure 7D:
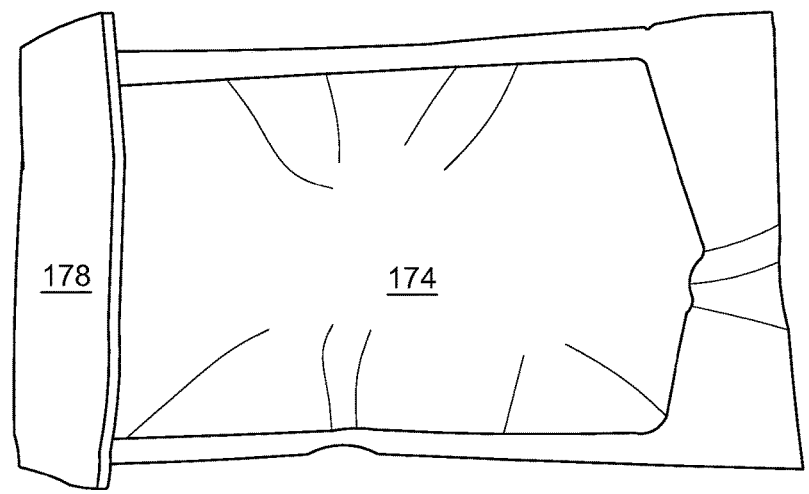

Referring to FIGS. 7C and 7D, in one embodiment, the fourth sealed end 178 of the pouch 174 is folded over so that it underlies a bottom panel of the pouch 174. The folded end of the pouch 174 may be rounded or pinched. The folded end of the pouch may have a fold line that is adjacent or abuts against the trailing ends of the top and bottom panels of the folder.

Figure 8A:
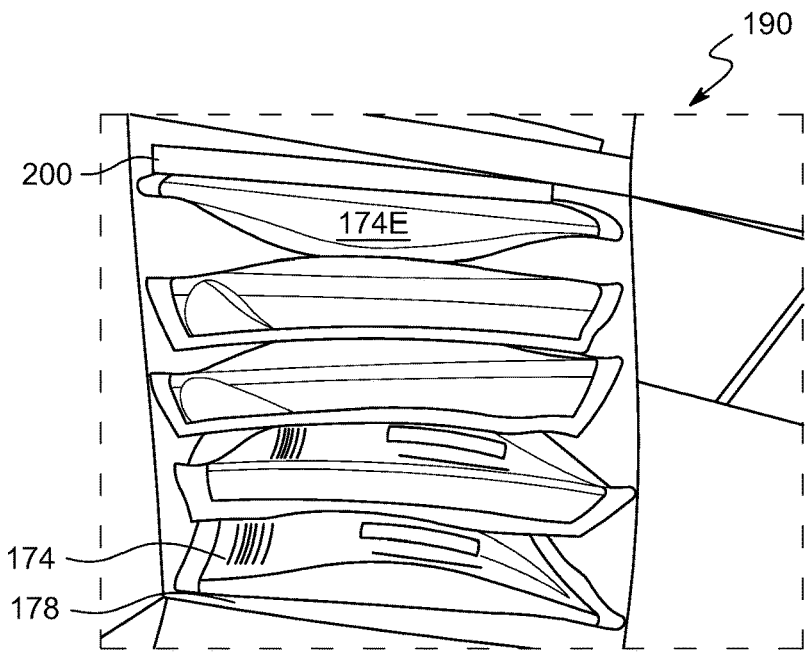
FIGS. 8A-8B show a method of packing sealed pouches containing medical devices into a carton with a foam insert, in accordance with one embodiment.
Figure 8B:
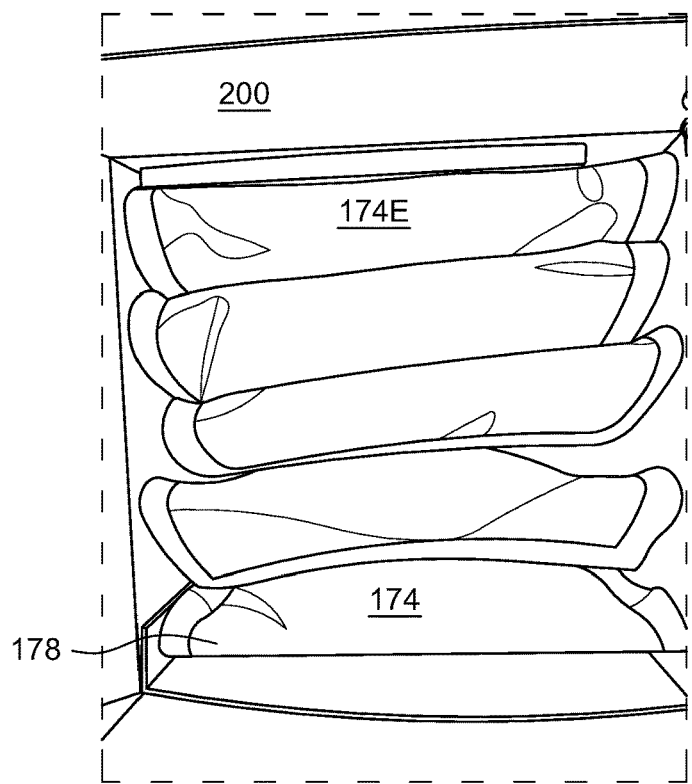

Referring to FIGS. 8A and 8B, in one embodiment, the folded ends 178 of the pouches 174 are inserted into the carton 190 so that the folded ends are adjacent the leading or front end of the main body of the sales unit carton. An IFU manual 200 may be positioned atop the final sealed pouch 174E loaded into the sales unit carton 190.

Figure 9A:
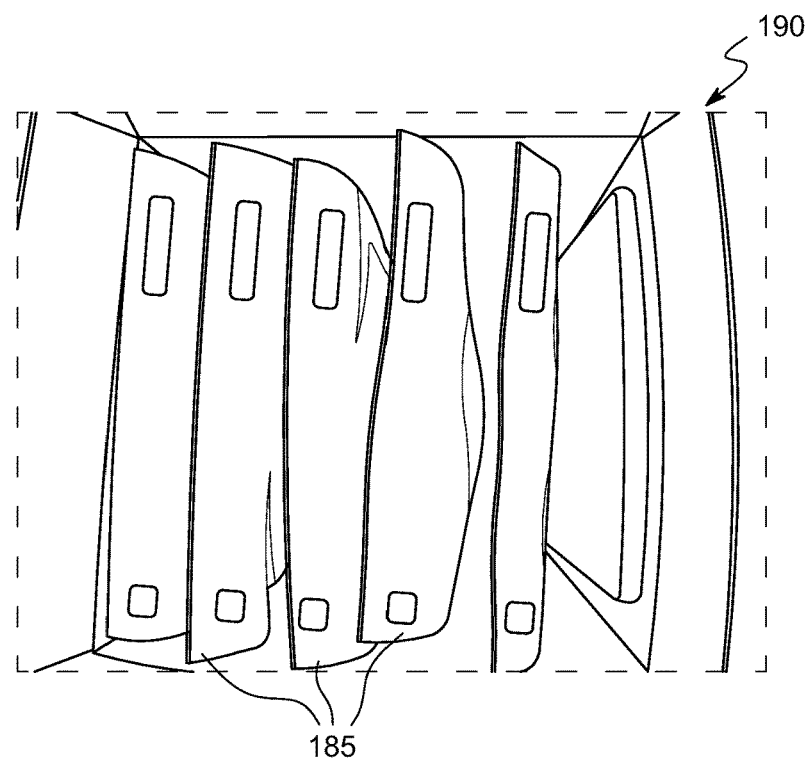
FIGS. 9A and 9B show a method of packing sealed pouches containing medical devices into a carton, in accordance with one embodiment.

Referring to FIG. 9A, in one embodiment, when the sealed pouches 174 are inserted into the carton 190, the pouch opening flanges 185 are positioned at the trailing or rear end of the carton. The pouch opening flanges are adjacent to the chevron shaped seal at the closed end of the pouches 174. In one embodiment, all of the pouch opening flanges 185 are curled in the same direction.

Figure 9B:
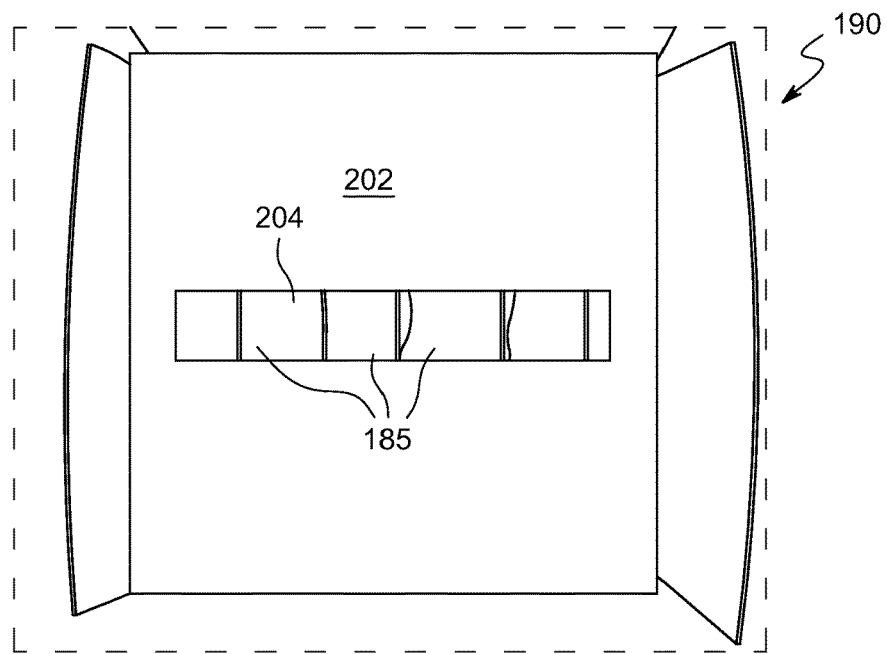

Referring to FIG. 9B, in one embodiment, the foam insert 202 having the elongated inspection window 204 is positioned atop the curled pouch opening flanges 185 of the individual sealed pouches. The elongated inspection window 204 enables packing personnel to confirm that all of the pouch opening flanges 185 are curled in the same direction. The elongated inspection window 204 also aligns with the apex of the chevron shaped seal of the pouch and the apex of the chevron shaped leading edges of the top and bottom panels of the folder. After the foam insert 202 has been placed atop the pouch opening flanges 185, the one or more closing flaps at the trailing end of the carton 190 may be closed.

Figure 10A:
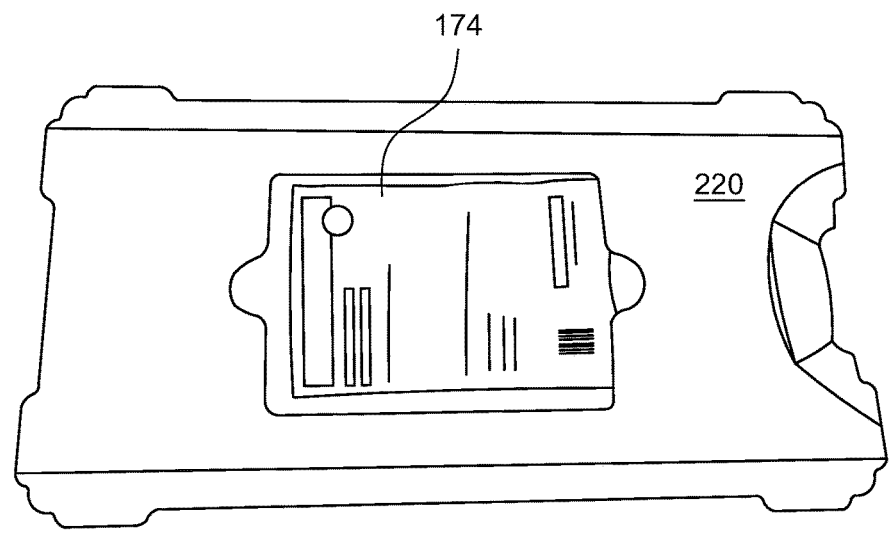
FIG. 10A shows a package for a medical device including a protective frame that encases a sealed pouch containing the medical device, in accordance with one embodiment.
Figure 10B:
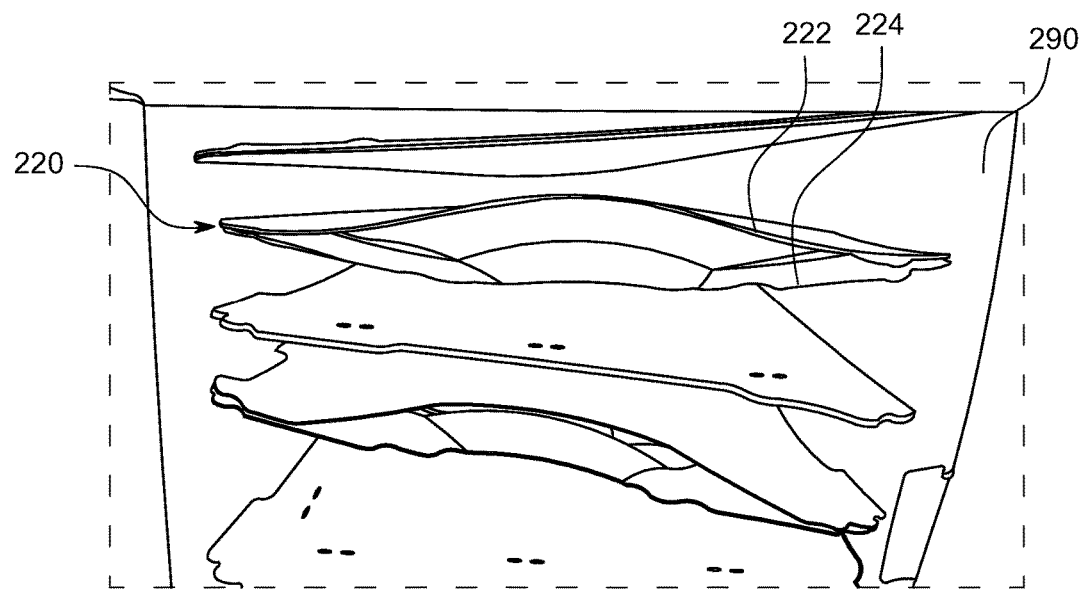
FIG. 10B shows a plurality of the packages shown in FIG. 10A inserted into a carton, in accordance with one embodiment of the invention.

Referring to FIGS. 10A and 10B, in one embodiment, a packaging system for a sealed pouch 174 may be disposed within a frame 220, such as a paperboard frame, having a top panel 222 and a bottom panel 224. The top and bottom panels 222, 224 at least partially encapsulate the upper and lower panels of the sealed pouch 174 to provide additional cushioning structure for supporting the sealed pouch from drop impacts. In one embodiment, a frame 220 encases each sealed pouch 174 to absorb drop impact shocks and secure pouches from wrinkle formation. Referring to FIG. 10B, in one embodiment, after the sealed pouches 174 have been loaded into the frames 220, the individual frames 220 containing the sealed pouches may be packed into a sales unit carton 290 that contains a plurality of stacked pouch/frame units.

Figure 11:
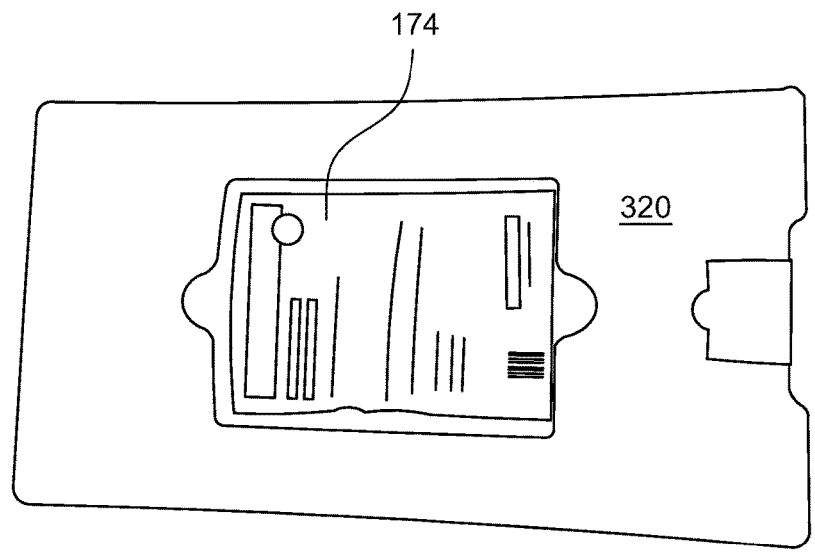
FIG. 11 shows a package for a medical device including a protective frame that encases a sealed pouch containing the medical device, in accordance with another embodiment.

Referring to FIG. 11, in one embodiment, a pouch 174 as disclosed and described herein may be supported by frame 320, such as a paperboard frame, that at least partially encapsulates the top and bottom panels of the sealed pouch 174 and at least partially surrounds the outer perimeter of the sealed pouch. In one embodiment, each sealed pouch is disposed within one of the pouch frames 320 disclosed in FIG. 11. The combination of the sealed pouch 174 and the pouch frame 320 may be stacked within a sale unit carton as disclosed herein.

Figure 12:
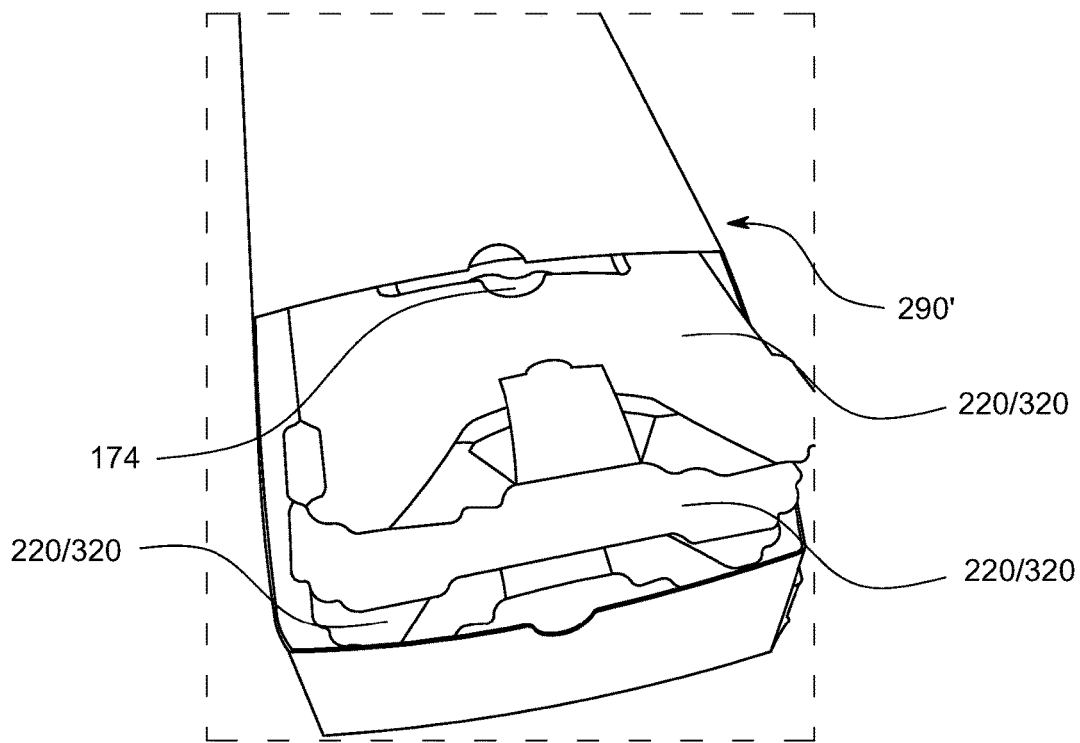
FIG. 12 shows a plurality of the packages shown in FIG. 11 inserted into a sales unit carton having a tear away front, in accordance with one embodiment.

Referring to FIG. 12, in one embodiment, the frames with sealed pouches may be loaded into a sales unit carton 290' having a tear away panel at a leading end. The tear away panel may be removed for obtaining access to the individual frames 220/320 containing sealed pouches 174 that are stacked within the sales unit carton 290'.

Figure 13A:
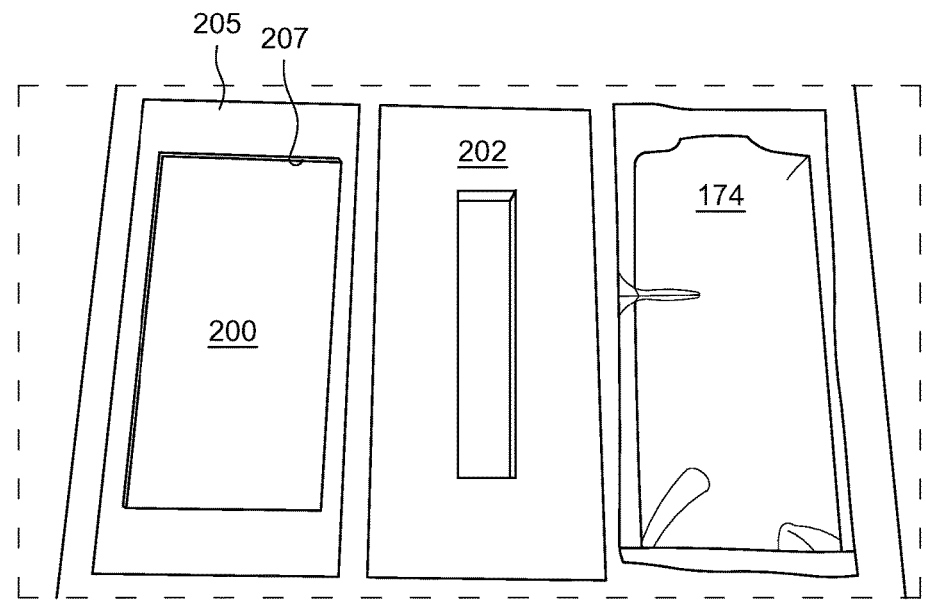
FIGS. 13A and 13B show a method of packing sealed pouches containing medical devices into a carton, in accordance with one embodiment.

Referring to FIG. 13A, in one embodiment, additional foam inserts may be utilized to support, cushion and protect the sealed pouches from drop impacts. In one embodiment, a series of foam inserts 202 are positioned above and below each sealed pouch 174. In one embodiment, a supplemental foam insert 205 having a central opening 207 receives an IFU manual 200 that is positioned at the top of the stack of sealed pouches and foam inserts.

Figure 13B:
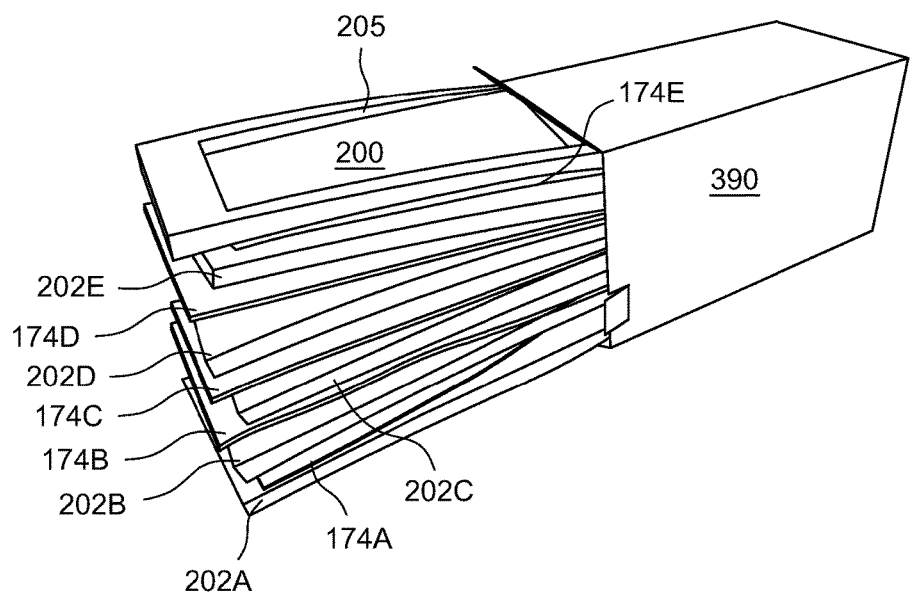

Referring to FIG. 13B, in one embodiment, a carton 390 has an opening at one end. A first foam insert 202 is inserted into the carton and a first sealed pouch 174A is positioned atop the first foam insert 202A. In one embodiment, the folded end of the first sealed pouch 174A is first inserted into the opening at the rear end of the carton 390 and the chevron sealed end of the first sealed pouch 174 trails. The foam inserts 202 and sealed pouches 174 are stacked atop another to form a stack including alternating foam inserts 202A and sealed pouches 174A-174E disposed therebetween. After all of the foam inserts 202A-202E and sealed pouches 174A-174E have been inserted into the carton 390, the supplemental foam insert 205 having the IFU manual 200 is inserted atop the stack. The flaps at the rear end of the carton 390 may then be closed for sealing the sales unit carton 390.

In one embodiment, the foam inserts may be joined together as a unitary structure having slots formed therein for inserting the sealed pouches into the slots. In one embodiment, a foam block may have slots formed therein for inserting the pouches into the slots.

Figure 14:
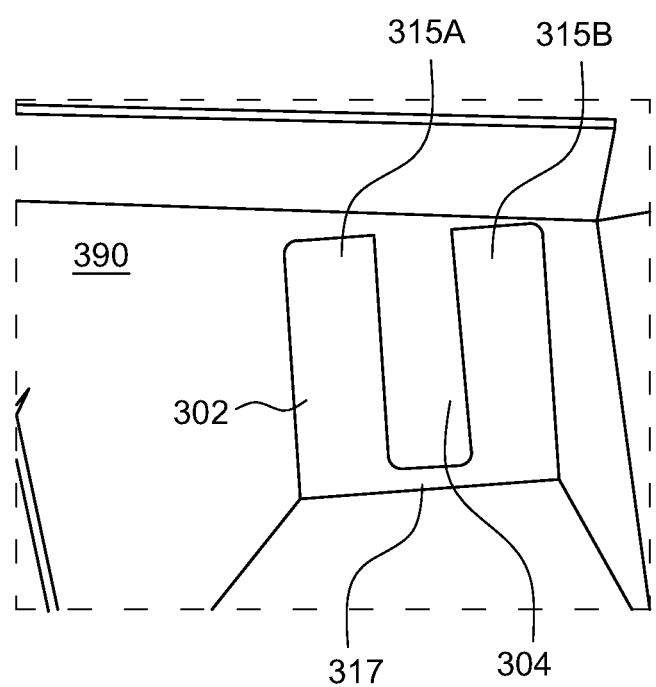
FIG. 14 shows a carton for sealed pouches containing medical devices, the carton having a foam insert to cushion the sealed pouches packed therein, in accordance with one embodiment.

Referring to FIG. 14, in one embodiment, a foam insert 302 an end of a carton 390 has a U-shaped opening 304 that extends to a peripheral edge of the foam insert 302. The U-shaped foam insert 302 has first and second vertically extending foam columns 318A, 318B that are interconnected at their bases by a foam base piece 317. In one embodiment, after the sealed pouches have been inserted into the carton 390, the foam insert 302 is positioned over the curled pouch opening flanges at the rear of the carton. The U-shaped opening 304 of the foam insert 302 is preferably aligned with the chevron shaped seal and the chevron shaped leading edges of the folders.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A package for a medical device comprising:
    a folder having a bottom panel and a top panel;
    said bottom panel including a leading edge, a trailing edge, and at least one medical device securing element;
    said top panel including a leading edge, and a trailing edge joined with said trailing edge of said bottom panel to define a folding line extending between said top and bottom panels, wherein said top panel has first and second lateral edges that extend along a length of said top panel from said leading edge of said top panel to said trailing edge of said top panel, and wherein said top panel has a first stress relieving slit that extends inwardly from said first lateral edge toward a center of said top panel, and a second stress relieving slit that extends inwardly from said second lateral edge toward the center of said top panel, and wherein said first and second stress relieving slits are aligned with one another along the length of said top panel, and wherein said folder has an unfolded configuration in which said leading edges of said top and bottom panels face in opposite directions, and a folded configuration in which said top panel is folded over said bottom panel at said folding line and said leading edges of said top and bottom panels face in the same direction and are aligned with one another.

2. The package as claimed in claim 1, wherein said bottom panel has first and second lateral edges that extend along a length of said bottom panel from said leading edge of said bottom panel to said trailing edge of said bottom panel, and wherein said bottom panel has a first stress relieving slit that extends inwardly from said first lateral edge toward a center of said bottom panel, and a second stress relieving slit that extends inwardly from said second lateral edge toward the center of said bottom panel, and wherein said first and second stress relieving slits of bottom panel are aligned with one another along the length of said bottom panel.

3. The package as claimed in claim 2, wherein when said folder is in the folded configuration, said first stress relieving slit of said top panel is aligned with said first stress relieving slit of said bottom panel and said second stress relieving slit of said top panel is aligned with said second stress relieving slit of said bottom panel.

4. The package as claimed in claim 3, wherein at least one of said stress relieving slits has an aperture at an inner end thereof.

5. The package as claimed in claim 3, wherein at least one of said stress relieving slits has an elliptical or ovoid shape, and wherein at least one of said stress relieving slits is rounded at one of said lateral edges.

6. The package as claimed in claim 1, further comprising a three-dimensional medical device secured on said bottom panel of said folder, wherein said top panel covers said three-dimensional medical device when said folder is in the folded configuration.

7. The package as claimed in claim 6, said bottom panel comprising said at least one medical device securing element secures said three-dimensional medical device to said bottom panel, wherein said at least one medical device securing element is connected with said bottom panel via a fold line that enables said at least one medical device securing element to be folded flat over said bottom panel or extended away from said bottom panel for engaging said three-dimensional medical device.

8. The package as claimed in claim 6, further comprising a pouch including two sheets of material that are joined together by a seal having a first leg that extends adjacent a leading end and second and third legs that extend adjacent first and second lateral sides of said pouch, wherein said first leg of said seal has a shape that matches the shape of said leading edges of said top and bottom panels of said folder.

9. The package as claimed in claim 8, wherein the first leg of said seal and said leading edges of said top and bottom panels have chevron shapes that match one another, wherein said folder is disposed in said pouch with the chevron shaped edges of said top and bottom panels abutting against said chevron shaped first leg of said seal of said pouch, and with said first lateral edges of said top and bottom panels abutting against said second leg of said seal and said second lateral edges of said top and bottom panels abutting against said third leg of said seal.

10. The package as claimed in claim 9, said seal further comprising a fourth leg extending between said second and third legs of said seal and adjacent a trailing end of said pouch for sealing said folder and said three-dimensional medical device within said pouch.

11. The package as claimed in claim 10, wherein said trailing end of said sealed pouch that includes said fourth leg of said seal is folded under said folder to define a pouch fold, and wherein said pouch fold abuts against said trailing edges of said top and bottom panels.

12. The package as claimed in claim 11, further comprising:
    a carton having a leading end and a trailing end;
    a plurality of said sealed pouches disposed within said carton, wherein each said sealed pouch has said pouch fold that is adjacent the leading end of said carton and said chevron shaped first leg of said seal that is positioned adjacent the trailing end of said carton.

13. The package as claimed in claim 8, wherein said pouch comprises a material selected from the group consisting of a foil polyester laminate, a foil nylon laminate, and heat sealable laminates.

14. The package as claimed in claim 1, wherein said folder comprises a material selected from the group of materials consisting of durable materials, smooth materials, paperboard, cardboard, and high density polyethylene (HDPE).

15. A package for a medical device comprising:
a sealed pouch having two sheets of material that are joined together by a seal having a first leg that extends adjacent a leading end of said pouch, second and third legs that extend adjacent first and second lateral sides of said pouch, and a fourth leg that extends adjacent a trailing end of said pouch;
a folder containing a medical device, said folder comprising a bottom panel and a top panel;
said bottom panel including a leading edge and a trailing edge,
said top panel including a leading edge, and a trailing edge joined with said trailing edge of said bottom panel to define a folding line extending between said top and bottom panels, wherein said top panel has first and second lateral edges that extend from said leading edge of said top panel to said trailing edge of said top panel, a first stress relieving slit that extends inwardly from said first lateral edge toward a center of said top panel, and a second stress relieving slit that extends inwardly from said second lateral edge toward the center of said top panel, wherein said top panel is folded over said bottom panel at said folding line so that said leading edges of said top and bottom panels face in the same direction and are aligned with one another, and wherein said folder is disposed in said sealed pouch with said leading edges of said top and bottom panels of said folder abutting against said first leg of said seal of said sealed pouch.

16. The package as claimed in claim 15, wherein said first leg of said seal has a chevron shape, and wherein said leading edges of said top and bottom panels have chevron shapes that match the chevron shape of said first leg of said seal.

17. The package as claimed in claim 16, wherein said bottom panel has first and second lateral edges that extend from said chevron shaped leading edge of said bottom panel to said trailing edge of said bottom panel, a first stress relieving slit that extends inwardly from said first lateral edge toward a center of said bottom panel, and a second stress relieving slit that extends inwardly from said second lateral edge toward the center of said bottom panel, wherein said first and second stress relieving slits are aligned with one another along the length of said bottom panel, and wherein outer ends of said first and second stress relieving slits are rounded at said respective first and second lateral edges of said bottom panel.

18. The package as claimed in claim 17, wherein said first and second stress relieving slits of said top panel are aligned with one another along a length of said top panel, and wherein outer ends of said first and second stress relieving slits of said top panel are rounded at said respective first and second lateral edges of said top panel.

19. The package as claimed in claim 18, wherein when said top panel is folded over said bottom panel said first stress relieving slit of said top panel is aligned with said first stress relieving slit of said bottom panel and said second stress relieving slit of said top panel is aligned with said second stress relieving slit of said bottom panel.

20. The package as claimed in claim 19, further comprising a three-dimensional medical device secured to said bottom panel of said folder, wherein said bottom panel of said folder comprises at least one medical device securing element for securing said three-dimensional medical device to said bottom panel of said folder, wherein said three-dimensional medical device has a section that defines a thickest portion of said three-dimensional medical device, and wherein said stress relieving slits on said top and bottom panels are aligned with the thickest portion of said three-dimensional medical device.

21. A package for a medical device comprising:
a folder having a top panel and a bottom panel;
said top panel including a leading edge and a trailing edge, said top panel having first and second lateral edges that extend along a length of said top panel between said leading edge of said top panel and said trailing edge of said top panel, wherein said top panel has a first stress relieving slit that extends inwardly from said first lateral edge toward a center of said top panel, and a second stress relieving slit that extends inwardly from said second lateral edge toward the center of said top panel;
said bottom panel including a leading edge and a trailing edge joined with said trailing edge of said top panel;
at least one medical device securing element provided on one of said top and bottom panels;
said folder having an unfolded configuration in which said leading edges of said top and bottom panels face in opposite directions, and a folded configuration in which said top panel is folded over said bottom panel and said leading edges of said top and bottom panels face in the same direction.

22. The package as claimed in claim 21, wherein said bottom panel has first and second lateral edges that extend along a length of said bottom panel between said leading edge of said bottom panel and said trailing edge of said bottom panel, wherein said bottom panel has a first stress relieving slit that extends inwardly from said first lateral edge toward a center of said bottom panel, and a second stress relieving slit that extends inwardly from said second lateral edge toward the center of said bottom panel, and wherein when said folder is in the folded configuration said first stress relieving slit of said top panel is aligned with said first stress relieving slit of said bottom panel and said second stress relieving slit of said top panel is aligned with said second stress relieving slit of said bottom panel.

* * * * *